United States Patent
Kadow et al.

(10) Patent No.: US 6,916,942 B2
(45) Date of Patent: Jul. 12, 2005

(54) PROCESS FOR THE PREPARATION OF C-4 CARBONATE TAXANES

(75) Inventors: John F. Kadow, Wallingford, CT (US); Harold Mastalerz, Guilford, CT (US); Joydeep Kant, Cherry Hill, NJ (US); Qiufen May Xue, Newbury Park, CA (US); James G. Tarrant, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/827,062

(22) Filed: Apr. 19, 2004

(65) Prior Publication Data

US 2004/0225009 A1 Nov. 11, 2004

Related U.S. Application Data

(62) Division of application No. 09/712,352, filed on Nov. 14, 2000, now Pat. No. 6,750,246.
(60) Provisional application No. 60/179,965, filed on Feb. 3, 2000.

(51) Int. Cl.$^7$ ............................................. C07D 305/14
(52) U.S. Cl. ....................... 549/510; 549/213; 549/214; 549/511
(58) Field of Search ................................ 549/510, 213, 549/214, 511

(56) References Cited

U.S. PATENT DOCUMENTS

| | | | |
|---|---|---|---|
| 5,283,253 A | 2/1994 | Holton et al. | 514/444 |
| 5,336,785 A | 8/1994 | Holton | 549/214 |
| 5,399,726 A | 3/1995 | Holton et al. | 549/510 |
| 5,466,834 A | 11/1995 | Holton | 549/510 |
| 5,705,508 A | 1/1998 | Ojima et al. | 514/320 |
| 5,739,359 A | 4/1998 | Kingston et al. | 549/358 |
| 5,767,296 A | 6/1998 | Terasawa et al. | 549/510 |
| 5,808,102 A | 9/1998 | Poss et al. | 549/220 |
| 5,840,929 A | 11/1998 | Chen | 549/510 |
| 5,840,931 A | 11/1998 | Bouchard et al. | 549/510 |
| 5,973,160 A | 10/1999 | Poss et al. | 548/110 |
| 6,100,411 A | 8/2000 | Ojima | 549/510 |
| 6,218,553 B1 | 4/2001 | Ojima | 549/510 |
| 6,248,908 B1 | 6/2001 | Kant | 549/510 |
| 6,350,887 B1 | 2/2002 | Thottathil et al. | 549/510 |
| 6,458,976 B1 | 10/2002 | Ojima | 549/510 |
| 6,515,151 B1 | 2/2003 | Poss et al. | 549/510 |
| 6,593,482 B2 | 7/2003 | Bouchard et al. | 549/510 |

FOREIGN PATENT DOCUMENTS

| | | |
|---|---|---|
| EP | 0 747 385 A1 | 12/1996 |
| EP | 0 764 643 A1 | 3/1997 |
| EP | 1 361 222 A1 | 11/2003 |
| WO | WO 94/14787 | 7/1994 |
| WO | WO 94/18164 | 8/1994 |

OTHER PUBLICATIONS

Shu–Hui Chen, Tetrahedron Letters, 37(23), pp. 3925–3938, 1996.
Shu–Hui Chen, et al, J. Med. Chem., 38, pp. 2263–2267, 1995.
Shu–Hui Chen, et al, J. Org. Chem., 59, pp. 6156–6158, 1994.
Shu–Hui Chen, et al, Bioorganic & Medicinal Chemistry Letters, 5(22), pp. 2741–2746, 1995.
A. Datta, et al, J. Med. Chem., 37, 4258–4260, 1994.
G. I. Georg, et al, Tetrahedron Letters, 35(48), pp. 8931–8934, 1994.
M. I. Nicoletti, et al, Proc. Am. Assoc. Cancer Res., 40, Abs. 1910, pp. 288, 1999.
G. Pratesi, et al, Proc. Am. Assoc. Cancer Res., Istituto Nazionale Tumori and Indena, 40, Abs. 1905, pp. 287, 1999.
D. Polizzi, et al, Cancer Research, 59(5), pp. 1036–1040, 1999.
G. Samaranayake, et al, Journal of Natural Products, 56(6), pp. 884–898, 1993.
K. Uoto, et al, Chem. Pharm. Bull., 45(12), pp. 2093–2095, 1997.

*Primary Examiner*—Ba K. Trinh
(74) *Attorney, Agent, or Firm*—Henry H. Gu

(57) ABSTRACT

A process for the preparation of novel C-4 carbonate taxanes useful as antitumor agents

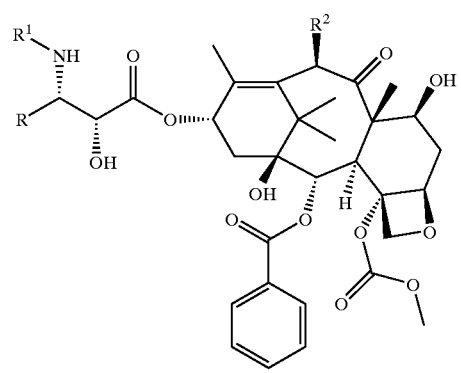

30 Claims, No Drawings

PROCESS FOR THE PREPARATION OF C-4 CARBONATE TAXANES

RELATED APPLICATION

This is division of application Ser. No. 09/712,352, filed on Nov. 14, 2000 now U.S. Pat. No. 6,750,246, which claims the priority of U.S. Provisional application No. 60/179,965, filed on Feb. 3, 2000.

FIELD OF THE INVENTION

The present invention concerns antitumor compounds. More particularly, the invention provides novel orally active paclitaxel derivatives, pharmaceutical formulations thereof, and their use as oral antitumor agents.

BACKGROUND ART

Paclitaxel is a natural product extracted from the bark of Pacific yew trees, *Taxus brevifolia* and the active constituent of the anticancer agent TAXOL®. It has been shown to have excellent antitumor activity in in vivo animal models, and recent studies have elucidated its unique mode of action, which involves abnormal polymerization of tubulin and disruption of mitosis. It is used clinically against a number of human cancers. It is an important cancer agent both therapeutically and commercially. Numerous clinical trials are in progress to expand and increase the utility of this agent for the treatment of human proliferative diseases. The results of TAXOL® clinical studies have been reviewed by numerous authors. A very recent compilation of articles by a number of different authors is contained in the entire issue of Seminars in Oncology 1999, 26 (1, Suppl 2). Other examples are such as by Rowinsky et al. in TAXOL®: A Novel Investigational Antimicrotubule Agent, J. Natl. Cancer Inst., 82: pp 1247–1259, 1990; by Rowinsky and Donehower in "The Clinical Pharmacology and Use of Antimicrotubule Agents in Cancer Chemotherapeutics," Pharmac. Ther., 52:35–84, 1991; by Spencer and Faulds in "Paclitaxel, A Review of its Pharmacodynamic and Pharmacokinetic Properties and Therapeutic Potential in the Treatment of Cancer," Drugs, 48 (5) 794–847, 1994; by K. C. Nicolaou et al. in "Chemistry and Biology of TAXOL®," Angew. Chem., Int. Ed. Engl., 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named docetaxel has also been found to have good antitumor activity and is the active ingredient of the commercially available cancer agent TAXOTERE®. See, Biologically Active Taxol Analogues with Deleted A-Ring Side Chain Substitutents and Variable C-2' Configurations, J. Med. Chem., 34, pp 1176–1184 (1991); Relationships between the Structure of Taxol Analogues and Their Antimitotic Activity, J. Med. Chem., 34, pp 992–998 (1991). A review of the clinical activity of TAXOTERE® by Jorge E. Cortes and Richard Pazdur has appeared in Journal of Clinical Oncology 1995, 13(10), 2643 to 2655. The structures of paclitaxel and docetaxel are shown below along with the conventional numbering system for molecules belonging to the class; such numbering system is also employed in this application.

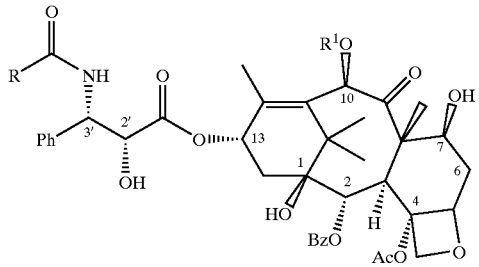

paclitaxel (TAXOL®): R=Ph; R'=acetyl
docetaxel (TAXOTERE®): R=t-butoxy; R'=hydrogen Ample evidence that paclitaxel has no oral activity can be found within the following quote from PCT patent application WO98/53811 by inventors Samuel Broder, Kenneth L. Duchin and Sami Selim and the references cited within the quote, which says: "Paclitaxel is very poorly absorbed when administered orally (less than 1%); see Eiseman et. al., Second NCI Workshop on Taxol and Taxus (September 1992); Suffness et. al. in *TAXOL Science and Applications* (CRC Press 1995). Eisemann et. al. indicate that paclitaxel has a bioavailability of 0% upon oral administration and Suffness et. al. report that oral dosing with paclitaxel did not seem possible since no evidence of antitumor activity was found on oral administration up to 160 mg mg/kg/day. Moreover, no effective method has been developed to enable the effective administration of oral paclitaxel (ie. a method of increasing the oral bioavailability of paclitaxel) or of other oral taxanes or paclitaxel analogs such as docetaxel which exhibit antitumor activity. For this reason, paclitaxel has not until now been administered orally to human patients, and certainly not in the course of treating paclitaxel-responsive diseases." Another report by J. Terwogt et. al. from The Lancet, Jul. 25, 1998, vol 352 page 285 also describes the low bioavailability of paclitaxel after oral dosing. In our own work, we have orally dosed paclitaxel to doses as high as 160 mg/kg/inj in murine (mouse) tumor models (sc M109) without signs of any efficacy and have concluded, like Suffness, that further dosing would not provide efficacy even though toxic doses were not reached. Furthermore, our own attempts to demonstrate activity for orally administered paclitaxel against human tumor xenografts implanted in either athymic mice or athymic rats have to date been unsuccessful.

The intention of this invention is to describe C-4 methyl carbonate taxane analogs which have surprising oral activity and thus would have utility against proliferative diseases after oral administration. Some of the background art pertaining to this invention are shown below.

Certain taxane derivatives with modifications at the C-4 hydroxy group have been described in the art.

U.S. Pat. No. 5,808,102 to Poss et al and PCT published patent application WO 94/14787 contain descriptions of taxane analogs with modifications at the C-4 positions.

Gunda I. Georg et. al describe the synthesis of a C-4 ester analog in *Tetrahedron Letters,* 1994, 35(48) 8931–8934.

S. Chen et. al. describe the synthesis of a C-4 cyclopropyl ester analog in *Journal of Organic Chemistry* 1994, 59(21), 6156–8.

U.S. Pat. No. 5,840,929 to Chen, Shu-Hui covering the C4 methoxy ether derivatives has issued on Nov. 24, 1998. A publication on the same topic has appeared:

Chen, Shu-Hui. First syntheses of C-4 methyl ether paclitaxel analogs and the unexpected reactivity of 4-deacetyl-4-methyl ether baccatin III. *Tetrahedron Lett.* 1996, 37(23), 3935–3938.

The following reference discusses a number of C-4 ester or carbonate analogs: Chen, Shu-Hui; Wei, Jian-Mei; Long, Byron H.; Fairchild, Craig A.; Carboni, Joan; Mamber, Steven W.; Rose, William C.; Johnston, Kathy; Casazza, Anna M.; et al. Novel C-4 paclitaxel (Taxol) analogs: potent antitumor agents. *Bioorg. Med. Chem. Lett.* 1995, 5(22), 2741–6.

The preparation of C-4 aziridinyl carbamate analogs has been described in: Chen, Shu-Hui; Fairchild, Craig; Long, Byron H. Synthesis and Biological Evaluation of Novel C-4 Aziridine-Bearing Paclitaxel (Taxol) Analogs. *J. Med. Chem.* 1995, 38(12), 2263–7.

The following papers describe reactions or transformations which are described as of potential for c-4 analog preparation:

A new method to modify the C-4 position of 10-deacetylbaccatin III. Uoto, Kouichi; Takenoshita, Haruhiro; Ishiyama, Takashi; Terasawa, Hirofumi; Soga, Tsunehiko. *Chem. Pharm. Bull.* 1997, 45(12), 2093–2095.

Samaranayake, Garnini; Neidigh, Kurt A.; Kingston, David G. I. Modified taxols, 8. Deacylation and reacylation of baccatin III. *J. Nat. Prod* 1993, 56(6), 884–98.

Datta, Apurba; Jayasinghe, Lalith R.; Georg, Gunda I. 4-Deacetyltaxol and 10-Acetyl-4-deacetyltaxotere: Synthesis and Biological Evaluation. *J. Med. Chem.* 1994, 37(24), 4258–60.

In spite of the abovementioned examples of C-4 analogs or methodology to prepare them, no evidence of orally active C-4 analogs has been supplied. Both TAXOL® and TAXOTERE® have no oral activity in human or animal models as mentioned in the following prior art described below on taxanes and oral modulators. Thus, the art to date does not suggest that C-4 taxanes should be different than other taxanes and therefore they should not be orally active. To the best of our knowledge, the art in no way specifically identifies any C-4 analogs which may have oral utility. The invention described in this patent application identifies novel C-4 analogs which due to their unique substitution surprisingly have oral activity.

The following references describe methods or possible methods for orally active taxanes.

Methods for administering taxanes in the presence of modulators have been reported to increase the amount of taxanes in the plasma after oral administration: Terwogt, Jetske M. Meerum; Beijnen, Jos H.; Ten Bokkel Huinink, Wim W.; Rosing, Hilde; Schellens, Jan H. M. Coadministration of cyclosporin enables oral therapy with paclitaxel. Lancet (1998), 352(9124), 285.

Terwogt, Jetske M. Meerum; Malingre, Mirte M.; Beijnen, Jos H.; Huinink, Wim W. ten Bokkel; Rosing, Hilde; Koopman, Franciska J.; Van Tellingen, Olaf; Swart, Martha; Schellens, Jan H. M. Coadministration of oral cyclosporin A enables oral therapy with paclitaxel. Clin. Cancer Res. (1999), 5(11), 3379–3384.

Hansel, Steven B. A method of making taxanes orally bioavailable by coadministration with cinchonine. PCT Int. Appl. WO 9727855 published Aug. 7, 1997.

Broder, Samuel; Duchin, Kenneth L.; Selim, Sami. Method and compositions for administering taxanes orally to human patients using a cyclosporin to enhance bioavailability. PCT Int. Appl. WO 9853811 published Dec. 3, 1998. These reports contain no antitumor efficacy data but the presence of taxanes in the plasma is extrapolated to show their potential for anticancer utility.

At least one report of oral activity of prodrugs in preclinical animal models has appeared in the prior art: Scola, Paul M.; Kadow, John F.; Vyas, Dolatrai M. Preparation of paclitaxel prodrug derivatives. Eur. Pat. Appl. EP 747385 published Dec. 11, 1996. The oral bioavailability of the prodrug which had oral efficacy was not disclosed and no further reports of these compounds progressing to man have appeared.

Very recently, an abstract describing a taxane analog (IDN-5109) with oral activity against tumors in mice was disclosed at the American Asssociation of Cancer Researchers in Philadelphia in 1999. The reference for the abstract is: Pratesi G, Polizzi D, Totoreto M, Riva A, Bombardelli E, Zunino F: IDN5109 a new taxane active after oral administration. Proc Am Assoc Cancer Res 1999 40 Abs 1905, Istituto Nazionale Tumori, 20133 Milan and Indena SpA, 20139, Milan, Italy. The structure of this compound is quite different than compounds described in the present invention. Unlike the compounds encompassed by the present invention, IDN-5109 is derived from 14-betahydroxy baccatin III and has an acetate on the hydroxy group at the C-4 position.

Two references on the iv activity of this compound are included for completeness.

Nicoletti M L, Rossi C, Monardo C, Stura S, Morazzoni P, Bombardelli E, Valoti G, Giavazzi R.: Antitumor efficacy of a paclitaxel analogue, IDN5109, on human ovarian carcinoma xenografts with different sensitivity to paclitaxel. Proc Am Assoc Cancer Res 1999 40 Abs 1910 [Evals+ citations].

Polizzi, Donatella; Pratesi, Graziella; Tortoreto, Monica; Supino, Rosanna; Riva, Antonella; Bombardelli, Ezio; Zunino, Franco. A novel taxane with improved tolerability and therapeutic activity in a panel of human tumor xenografts. *Cancer Res.* 1999, 59(5), 1036–1040.

Paclitaxel is a highly schedule dependent drug that benefits traditionally from prolonged tumor exposure times. This relates to paclitaxel's mechanism of action as taxanes only recognize and bind to the polymerized state of tubulin which occurs only during a brief period of the cancer cell cycle. The currently used intravenous infusions (1–3 hours) are now readily accepted and efficacious and preclude the routine use of protracted (>24 hours) continuous schedules. However, an oral taxane may provide a compliant and cost effective way of accomplishing such extended duration of exposure. Recently, clinical utility has also been demonstrated using repetitive once weekly administrations of moderate (i.e., other than maximally tolerated) doses of TAXOL® and an oral taxane would be ideal for such protracted regimens. Other purported clinical indications for taxanes use (e.g., rheumatoid arthritis, multiple sclerosis) would also benefit from the availability of an oral taxane. An orally administered effective taxane would offer both an attractive alternative from the parenteral format of current clinical taxane usage, and a potential therapeutic advantage because of the many avenues of scheduling yet to be investigated.

Thus it is clear there is a great need to identify taxanes with both good oral bioavailability and good oral efficacy, which are comparable to paclitaxel administered parenterally.

SUMMARY OF INVENTION

This invention relates to novel antitumor compounds represented by formula I, or pharmaceutically acceptable salts thereof:

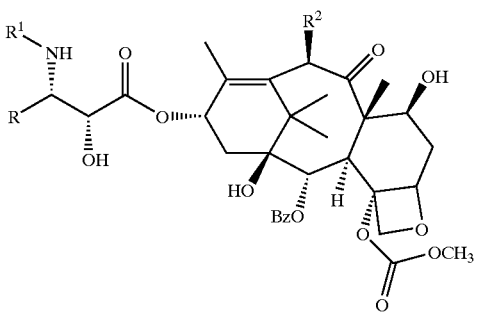

wherein:

R is phenyl, isopropyl, or tert butyl;
$R^1$ is —C(O)$R^Z$ in which $R^Z$ is $(CH_3)_3CO$—, $(CH_3)_3CCH_2$—, $CH_3(CH_2)_3O$—, cyclobutyl-, cyclohexyloxy, or (2-furyl);
$R^2$ is $CH_3C(O)O$—.

Another aspect of the present invention provides a method for inhibiting tumor growth in a mammalian host which comprises administering to said mammalian host an antitumor effective amount of a compound of formula I, or its pharmaceutically acceptable salts. Preferably, the method of administration is oral.

Yet, another aspect of the present invention provides a pharmaceutical formulation which comprises an antitumor effective amount of a compound of formula I, or its pharmaceutically acceptable salts, in combination with one or more pharmaceutically acceptable carriers, excipients, diluents or adjuvants.

DETAILED DESCRIPTION OF THE INVENTION

In this disclosure of the invention, unless otherwise specified explicitly or in context, the following definitions apply. In this application, the symbols once defined retain the same meaning throughout the application, until they are redefined.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl. As used herein t-butyloxy and t-butoxy are used interchangeably.

"Aryl" means aromatic hydrocarbon having from six to ten carbon atoms; examples include phenyl and naphthyl. "Substituted aryl" means aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, cyano, azido, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but are not limited to, ethers such as methyl, t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether, dialkyl alkoxy silyl ethers such as diisopropyl methoxy silyl ethers; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis, 3rd Ed., 1999, John Wiley & Sons, New York.

"Ph" means phenyl; "ipr" means isopropyl;

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

A preferred embodiment are compounds I, or pharmaceutically acceptable salts thereof which are depicted in Table I below.

TABLE I

| Orally Active C-4 Methyl Carbonate Taxanes | | | |
|---|---|---|---|
| Compound | R | $R^1$ | $R^2$ |
| Ia | $(CH_3)_3C$— | $(CH_3)_3COC(O)$— | $CH_3C(O)O$— |
| Ib | $(CH_3)_2CH$— | $(CH_3)_3COC(O)$— | $CH_3C(O)O$— |
| Ic | Phenyl- | $(CH_3)_3CCH_2C(O)$— | $CH_3C(O)O$— |
| Id | Phenyl- | CyclobutylC(O)— | $CH_3C(O)O$— |
| Ie | $(CH_3)_3C$— | CyclohexylOC(O)— | $CH_3C(O)O$— |
| If | $(CH_3)_3C$— | $(CH_3)_3CCH_2C(O)$— | $CH_3C(O)O$— |
| Ig | Phenyl- | $(CH_3)_3COC(O)$— | $CH_3C(O)O$— |
| Ih | Phenyl- | $CH_3(CH_2)_3OC(O)$— | $CH_3C(O)O$— |
| Ij | $(CH_3)_3C$— | CyclobutylC(O)— | $CH_3C(O)O$— |
| Ik | $(CH_3)_3C$— | (2-furyl)C(O)— | $CH_3C(O)O$— |

An even more preferred embodiment are compounds I, or pharmaceutically acceptable salts thereof which are shown in Table II.

TABLE II

| Compound | R | $R^1$ | $R^2$ |
|---|---|---|---|
| Ia | $(CH_3)_3C$— | $(CH_3)_3COC(O)$— | $CH_3C(O)O$— |
| If | $(CH_3)_3C$— | $(CH_3)_3CCH_2C(O)$— | $CH_3C(O)O$— |

TABLE II-continued

| Compound | R | R¹ | R² |
|---|---|---|---|
| Ij | (CH₃)₃C— | CyclobutylC(O)— | CH₃C(O)O— |
| Ik | (CH₃)₃C— | (2-furyl)C(O)— | CH₃C(O)O— |

The new compounds that have the general formula I display a significant inhibitory effect with regard to abnormal cell proliferation, and have therapeutic properties that make it possible to treat patients who have pathological conditions associated with an abnormal cell proliferation. In addition, these compounds possess significant oral bioavailability and thus can elicit their positive therapeutic effects after being administered orally.

The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas.

The novel compounds in accordance with the invention are particularly useful in the treatment of non-Hodgkin's lymphoma, multiple myeloma, melanoma, and ovarian, urothelial, oesophageal, lung, and breast cancers. The compounds can be utilized to prevent or delay the appearance or reappearance, or to treat these pathological conditions. The compounds may be used as antiangiogenesis inhibitors for both anticancer activities or for abnormal wound healing or other hyperproliferative diseases dependent on blood vessel formation.

In addition, the compounds of formula I are useful in treating and/or preventing polycystic kidney diseases (PKD) and rheumatoid arthritis. The compounds of this invention may also be useful for the treatment of Alzheimer's or Parkinson's disease or multiple sclerosis. While some of the products of general formula I are of interest due to advantages over commercial taxanes following iv administration, their main attribute is due to their unique properties after oral administration.

The compounds of this invention can be made by techniques from the conventional organic chemistry repertoire. Schemes 1–3, which depict processes that compounds within the scope of formula I can be made, are only shown for the purpose of illustration and are not to be construed as limiting the processes to make the compounds by any other methods.

A compound of formula I may be produced by the processes as depicted in Schemes 1–3 which follow. The methods can be readily adapted to variations in order to produce compounds within the scope of formula I but not specifically disclosed. Further variations of the methods to produce the same compounds in somewhat different fashion will also be evident to one skilled in the art. The numbering on baccatin III derivative of formula II as used in this application is as shown in the initial taxane structure.

One of the ways the compounds of this invention can be made is by the general method which shown is Scheme 1. In Step (a) of the scheme, azetidinone IV is reacted with a compound of formula II (a baccatin III derivative). The general class of azetidinones (β-lactams) of formula IV are well known. Methods for preparing suitably substituted β-lactams can be found in U.S. Pat. No. 5,175,315, European patent application 0 590 267 A2, the other U.S. patents or literature mentioned above, or references therein by Ojima et al. in Tetrahedron, 48, No. 34, pp 6985–7012 (1992); Journal of Organic Chemistry, 56, pp 1681–1683 (1991); and Tetrahedron Letters, 33, No. 39, pp 5737–5740 (1992); by Brieva et al. in J. Org. Chem., 58, pp 1068–1075; by Palomo et al. in Tetrahedron Letters, 31, No. 44, pp 6429–6432 (1990); and in Rey, Allan W.; Droghini, Robert; Douglas, James L.; Vemishetti, Purushotham; Boettger, Susan D.; Racha, Saibaba; Dillon, John L. Can. J. Chem. 72(10), 2131–6 (1994).

All disclosures are herein incorporated by reference in their entirety. The methods that can be adapted to variations in order to produce other azetidinones within the scope of formula IV, but not specifically disclosed herein or in the above references or reported elsewhere, will be obvious to anyone skilled in the art.

The baccatin III derivatives (II) can be attached to a sidechain using any of the methodology which is now already well known in the art. The many references cited in this invention disclosure and Tetrahedron, 48, No. 34, pp 6985–7012 (1992) describe processes whereby the class of azetidinones of formula IV are reacted with (C)13-hydroxy group of baccatin III derivatives or metal alkoxide thereof to afford taxane analogues with a variety of (C)13-side chains. In Step (a) of Scheme 1, it is advantageous to convert the hydroxy group on the (C)13-carbon into a metal alkoxide before the coupling. The formation of a desired metal alkoxide may be done by reacting a compound of formula II with a strong metal base, such as lithium diisopropylamide, C1–6 alkyllithium, lithium or sodium or potassium bis (trimethylsilyl)amide, phenyllithium, sodium hydride, potassium hydride, lithium hydride, or the like base. For example when lithium alkoxide is desired, a compound of formula II may be reacted with n-butyllithium in an inert solvent such as tetrahydrofuran. For examples of attachment of substituted baccatins with a suitably substituted lactam via the method of Holton see U.S. Pat. No. 5,175,315; U.S. Pat. No. 5,466,834; U.S. Pat. No. 5,229,526; U.S. Pat. No. 5,274,124; U.S. Pat. No. 5,243,045; U.S. Pat. No. 5,227,400; U.S. Pat. No. 5,336,785, and U.S. Pat. No. 5,254,580, U.S. Pat. No. 5,294,637, or EP 0 590 267 A2. Some examples of using β-lactams to prepare other substituted taxane derivatives are in PCT WO94/14787. This patent also describes an alternative method for attaching substituted isoserine sidechains to substituted baccatins which would be applicable for the compounds of this invention. This same alternate method is described in another publication by Kingston et. al. Tetrahedron Lett. (1994), 35(26), 4483–4. Further information on alternative methods to attach sidechains to baccatins are contained in Thottathil, et. al Eur. Pat. Appl. EP 735036 published Oct. 2, 1996.

Scheme 1

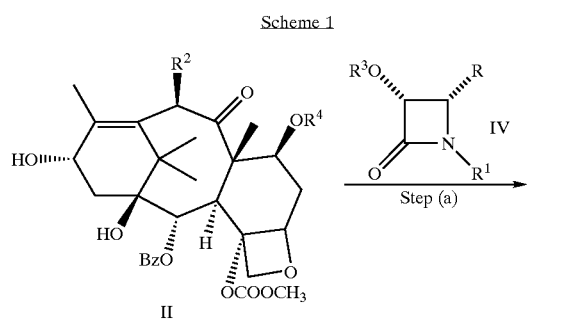

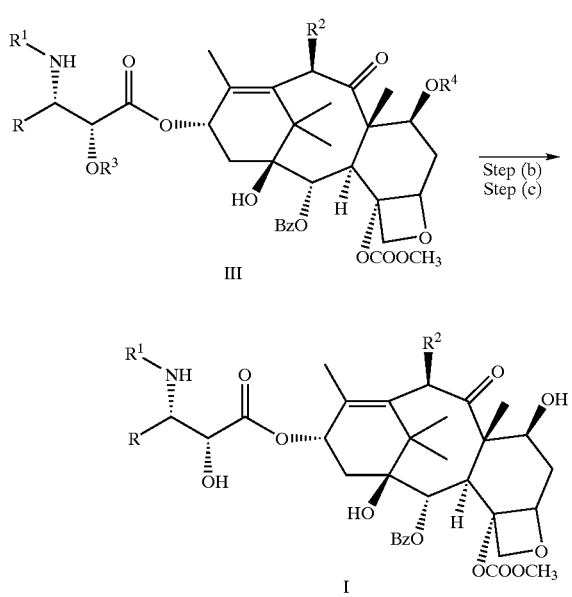

Scheme 2

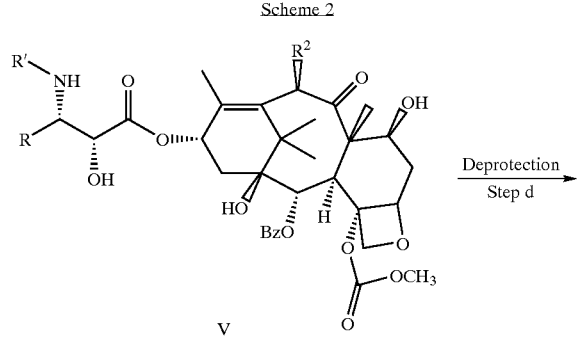

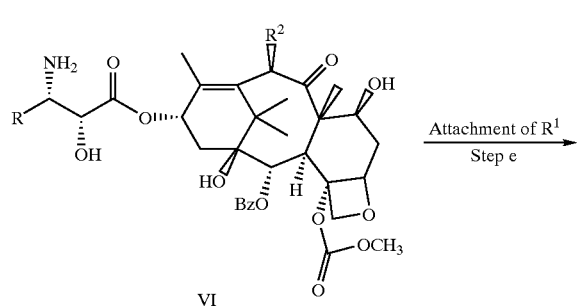

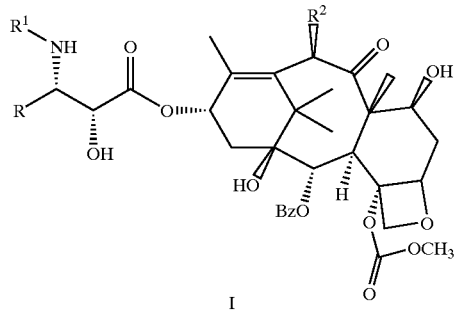

As used herein, $R^3$ and $R^4$ are conventional hydroxy protecting groups. Conventional hydroxy protecting groups are moieties which can be employed to block or protect a hydroxy function, and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 1-methyl-1-methoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether, dialkyl alkoxy silyl ethers such as diisopropyl methoxy silyl ethers; 2,2,2-trichloroethyoxymethyl, 2,2,2-trichloroethyloxycarbonyl (or simply trichloroethyloxycarbonyl), benyloxycarbonyl and the like. Other suitable hydroxy protecting groups which may be used are found in Chapter 2 of "Protecting Groups in Organic Synthesis", Third Ed., by Theodora W. Greene and Peter G. M. Wuts (1999, John Wiley & Sons, New York). A protecting group for formula IV compounds which has been used frequently in the literature is trialkylsilyl. Most preferred groups for $R^3$ include 1-methyl-1-methoxyethyl (MOP), a trialkyl silyl ether, or a dialkyl alkoxy silyl ether such as a diisopropyl methoxy silyl ether. The most preferred group for $R^4$ is a dialkyl alkoxy silyl ether such as a diisopropyl methoxy silyl ether but a trialkyl silyl ether or a carbonate such as a benzyl carbonate might also be preferred. In Step (b), the protecting group $R^3$ or R4 or possibly both are removed. If $R^3$ or $R^4$ are silyl based protecting groups, removal is effected by triethylamine trihydrofluoride in THF solvent. Other fluoride sources could also be utilized. For example tetrabutyl ammonium fluoride, pyridinium hydrofluoride, potassium fluoride, or cesium fluoride may find utility. The potassium fluoride may be utilized in combination with a complexing agent such as 18-crown-6 or the like to aid in desilylation. A solvent such as acetonitrile is typically used under these conditions. Other conditions such as mild aqueous hydrochloric acid or trifluoroacetic acid and a cosolvent such as acetonitrile or THF may be useful for deprotection of the silyl groups. The same acidic conditions work well to remove the 1-methyl-1-methoxyethyl (MOP) protecting group.

The conditions actually employed will depend on the protecting groups employed for $R^3$ and $R^4$. For example one preferred route might employ a MOP group for $R^3$ and a diisopropyl methoxy silyl ether for $R^4$. In this case, step b would entail a mild acidic workup using aqueous hydrochloric acid and an organic solvent. The resulting 2' deprotected compound would be exposed to a fluoride source such as triethylamine trihydrofluoride in THF solvent in step c to produce compound I after chromatographic or crystallographic purification.

Scheme 3
Preferred Synthesis of Protected C-4 Methyl Carbonate Baccatin

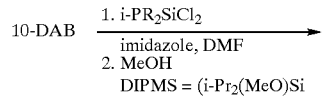

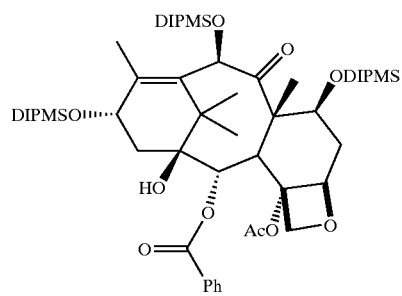 

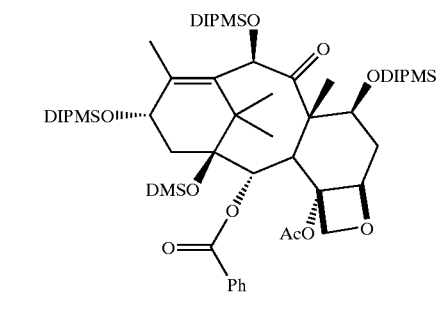 

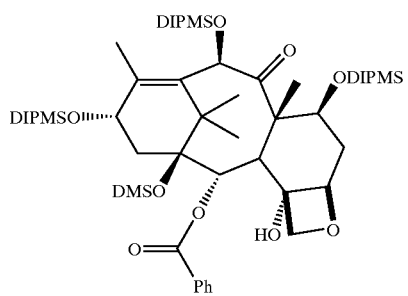 

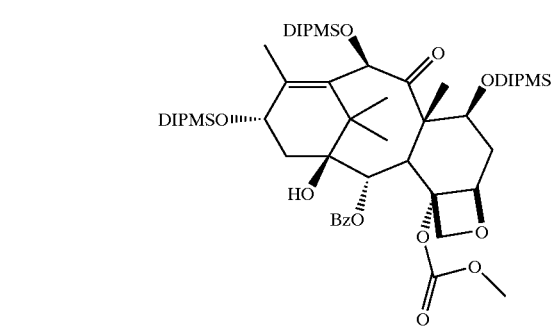

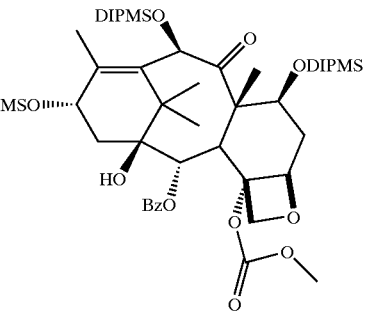 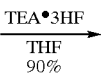

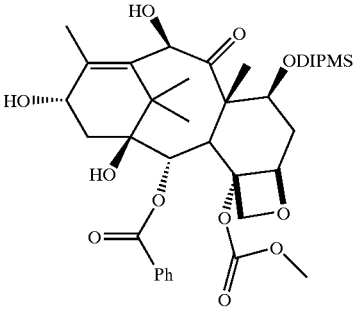 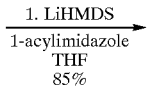

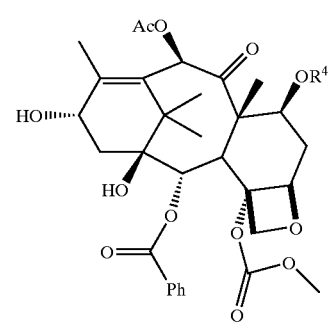

II
$R^4$ = DIPMS

Another aspect of the invention involves the synthesis of compounds I with novel substituents $R^2$ at the C-10 position. These compounds can be prepared by attaching an alternative ester rather than the acetate ester group which is attached in Scheme 3.

An alternative preparation of compounds I is depicted in Scheme 2. It involves the conversion of one compound V in which R' forms a nitrogen protecting group such as tBuO (CO)-(tBoc) or PhCH2OC(O)-(CBZ). The groups can be removed by acidic hydrolysis or in the case of CBZ by hydrogenolysis. The preparation of the amine intermediate VI is described in the examples and is carried out by methodology which is well known in the art. The amine intermediate VI is dissolved in an inert solvent such as ethyl acetate and a base such as sodium bicarbonate is added. A stoichiometric or slightly greater amount of most preferably an acid chloride, chloroformate or, alternatively, acid anhydride is added to provide compound I directly.

The preparation of the baccatin derivatives of structure II (as shown in Scheme 1 where $R^2$ is AcO—) is shown in Scheme 3 and illustrated in Preparation 7. The specific examples that follow illustrate the syntheses of the compounds of the instant invention, and are not to be construed as limiting the invention in sphere or scope. The method may be adapted to variations in order to produce the compound embraced by this invention but not specifically disclosed. Further, variations of the methods to produce the same compound in a somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-d6 (deuterated acetone). DMSO-d6 (perdeuterodimethylsulfoxide), D2O (deuterated water), $CDCl_3$ (deuterochloroform) and other conventional deuterated solvents. The infrared (IR) spectral description include only absorption wave numbers (cm-1) having functional group identification value.

Celite is a registered trademark of the Johns-Manville Products Corporation for diatomaceous earth.

Silica gel used in the following experimentals is silica gel 60 with a particle size 230–400 mesh obtained from EM Separations Technology.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); (DHQ)2PHAL (hydroquinine 1,4-phthalazinediyl diether). Tf=triflate=trifluoromethanesulfonate; LRMS (low resolution mass spectrometry); ESI (electrospray ionization); TEMPO (2,2,6,6-tetramethyl-1-piperidinyloxy, free radical); DBU (diazobicycloundecene); MOMCl (chloromethyl methyl ether); Ac (acetyl); (Ar, aryl); Bz (benzoyl); Cbz (benzyloxycarbonyl); DCI (desorption chemical ionization); DMF (dimethylformamide); FAB (fast atom bombardment); H (hour(s)); HRMS (high resolution mass spectrometry); LiHMDS (lithium hexamethyldisilazane or lithium bis (trimethylsilyl)amide); HMDS (hexamethyldisilazane); i-PrOH (isopropylalcohol); min (minute(s)); MS (mass spectrometry); Ph (phenyl); rt (room temperature); tBu (tertiarybutyl); TES (triethylsilyl), TLC (thin layer chromatography) Y (yield) TPAP (tetrapropyl ammonium peruthenate); MCPBA (meta chloroperoxy benzoic acid); LDA (lithium diisopropyl amide); TBS (tert-butyl-dimethylsilyl); 18-crown-6 (1,4,7,10,13,16-hexaoxacyclo-octadecane); DEAD (diethylazodicarboxylate); Red-Al® (Aldrich Catalogue) is $65^+$ weight % solution of sodium bis(2-methoxyethoxy)aluminum hydride in toluene; DCM means dichloromethane; "sat." means saturated.

PREPARATIONS

Preparation 1

(±)-cis-4-tert-Butyl-1-tert-butyloxycarbonyl-3-triethylsilyloxy-azetidin-2-one

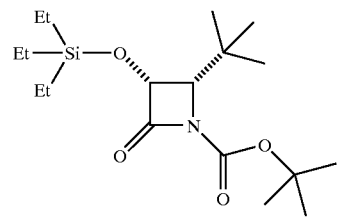

Trimethylacetaldehyde (20.3 mL, 1.25 equiv) was added to a strirred suspension of p-anisidine (18.4 gm, 0.150 mole) and anhydrous $Na_2SO_4$ (150 gm) in anhydrous DCM (250 mL) at RT. After 2 hr, this was filtered and the solid was washed with additional anhydrous DCM. The solvent was removed from the filtrate and the crystalline residue was dissolved in anhydrous DCM (750 mL) and placed under a nitrogen atmosphere. Triethylamine (48.0 mL, 2.3 equiv) was added and the reaction was cooled to −78° C. Benzyloxyacetyl chloride (27.2 mL 1.15 equiv) was added dropwise and then the reaction was allowed to warm to RT. After 24 hr, this was washed with 0.5 M HCl (twice), sat. aqueous $NaHCO_3$ solution, brine and dried ($Na_2SO_4$). The solvent was removed and the residue was chromatographed on a silica gel column (gradient elution with 20% DCM in hexane containing 0 to 20% EtOAc) to afford (±)-cis-4-tert-butyl-3-benzyloxy-1-p-methoxybenzyl-azetidinone as a crystalline solid (46.9 gm, 92%): $^1$H NMR ($CDCl_3$) δ 1.09 (s, 9H), 3.81 (s, 3H), 4.15 (d, 1H, J=5.5 Hz), 4.77 (d, 1H, J=11.9 Hz), 4.81 (d, 1H, J=5.5 Hz), 5.03 (d, 1H, J=11.9 Hz) 6.87–7.43 (m, 9 Hz); LRMS (ESI) 340 ([M+H]$^+$). A solution of ceric ammonium nitrate (60.4 gm 3.6 equiv) in 900 mL of water was added to a well stirred solution of the azetidinone (10.38 gm, 30.6 mmole) in acetonitrile (600 mL) in an ice bath over 1 hr. The reaction was then extracted with EtOAc (twice) and the combined organic extracts were washed with sat. aqueous $NaHCO_3$ solution (twice), 20% aqueous $NaHSO_3$ solution, sat. aqueous $NaHCO_3$ solution and brine. After being dried ($Na_2SO_4$), the solvents were removed and the residue was chromatographed on a silica gel column (gradient elution with portions of hexane containing 10 to 40% EtOAc) to afford 5.64 gm of slightly impure (±)-cis-3-benzyloxy-4-tert-butyl-azetidin-2-one: $^1$H NMR (CDCl$_3$) δ 1.04 (s, 9H), 3.51 (d, 1H, J=5.2 Hz), 4.71 (m, 2H), 4.96 (d, 1H, J=11.9 Hz) 6.10 (brs, 1H), 7.35 (m, 5H). A suspension of this material (5.54 gm, 23.8 mmole) and 2.5 gm of 10% Pd on charcoal in absolute EtOH (100 mL) was hydrogenated (34 psi H$_2$, Parr apparatus) for 23 hr. A further 2 gm of the Pd catalyst was added and the hydrogenation was continued for a further 17 hr at 50 psi H$_2$. The catalyst was removed by filtration and the solvent was removed from the filtrate to leave crude (±)-cis-3-hydroxy-4-(tert-butyl)-azetidin-2-one: $^1$H NMR (CDCl$_3$+1 drop D$_2$O) δ 1.05 (s, 9H), 3.48 (d, 1H, J=5.0 Hz), 4.98 (d, 1H, J=5.0 Hz). This material was dissolved in dry DMF (40 mL) and imidazole (3.24 gm, 2 equiv) and triethylsilyl chloride (4.0 mL, 1 equiv) were added. After 10 min, the reaction was partitioned between water and a mixture of EtOAc and hexane (1:1). The organic phase was washed with water (twice), brine and then dried (Na$_2$SO$_4$). The solvents were removed and the residue was chromatographed on a silica gel column (gradient elution with 20 to 25% EtOAc in hexane) to give (±)-cis-4-tert-butyl-3-triethylsilyloxy-azetidin-2-one (3.86 gm): $^1$H NMR (CDCl$_3$) δ 0.70 (m, 6H), 0.98 (m, 18H), 3.39 (d, 1H, J=5.0 Hz), 4.88 (dd, 1H, J=2.1, 5.0 Hz), 6.08 (brs, 1H). A solution of this azetidinone (2.04 gm, 7.92 mmole), diisopropylethyl amine (1.66 mL, 1.2 equiv), di-tert-butyl dicarbonate (1.90 gm, 1.1 equiv) and p-dimethylaminopyridine (194 mg, 0.2 equiv) in dry DCM (24 mL) was left stirring at RT for 3 hr. The reaction was diluted with DCM, washed with brine and dried (Na$_2$SO$_4$). Removal of the solvent followed by silica gel column chromatography (gradient elution with 0 to 20% EtOAc in hexane) afforded 2.71 gm (96%) of the title compound as an oil: $^1$H NMR (CDCl$_3$) δ 0.70 (m, 6H), 1.00 (m, 9H), 1.09 (s, 9H), 1.53 (s, 9H), 3.90 (d, 1H, J=6.5 Hz), 4.93 (d, 1H, J=6.5 Hz).

Preparation 2

(±)-cis-1-tert-butyloxycarbonyl-4-iso-propyl-3-triethylsilyloxy-azetidin-2-one

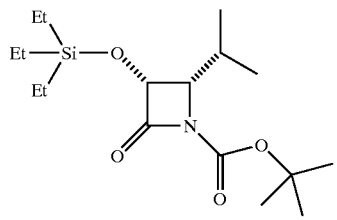

Isobutyraldehyde (4.62 mL, 1.25 equiv) was added to a strirred suspension of p-anisidine (5.00 gm, 40.7 mmole) and anhydrous Na$_2$SO$_4$ (25 gm) in anhydrous DCM (80 mL) at RT. After 1 hr, this was filtered and the solid was washed with additional anhydrous DCM. The solvent was removed from the filtrate and the residue was dissolved in anhydrous DCM (200 mL) and placed under a nitrogen atmosphere. Triethylamine (13.1 mL, 2.3 equiv) was added and the reaction was cooled to −78° C. Acetoxyacetyl chloride (5.00 mL 1.15 equiv) was added dropwise and the reaction was allowed to warm to RT. After 20 hr, this was washed with 0.5 M HCl (twice), sat. aqueous NaHCO$_3$ solution, brine and dried (Na$_2$SO$_4$), the solvent was removed and the residue was chromatographed on a silica gel column (gradient elution with 20 to 30% EtOAc in hexane) to afford (±)-cis-3-acetoxy-4-isopropyl-1-p-methoxybenzylazetidin-2-one as a solid (7.15 gm, 63%): $^1$H NMR (CDCl$_3$) δ 0.99 (d, 3H, J=7.0 Hz), 1.02 (d, 3H, J=7.0 Hz), 2.20 (s, 3H), 3.82 (s, 3H), 4.24 (t, 1H, J=5.6 Hz), 6.06 (d, 1H, J=5.3 Hz), 6.88–7.38 (m, 4H). A solution of ceric ammonium nitrate (51.3 gm 3.6 equiv) in 750 mL of water was added to a well stirred solution of the azetidinone (7.20 gm, 26.0 mmole) in acetonitrile (500 mL) in an ice bath over 1 hr. The reaction was then extracted with EtOAc (twice) and the combined organic extracts were washed with sat. aqueous NaHCO$_3$ solution (twice), 20% aqueous NaHSO$_3$ solution, sat. aqueous NaHCO$_3$ solution and brine. After being dried (Na$_2$SO$_4$) the solvents were removed to leave 4.26 gm of crude (±)-cis-3-acetoxy-4-iso-propyl-azetidin-2-one: $^1$H NMR (CDCl$_3$) δ 0.86 (d, 3H, J=6.6 Hz), 0.99 (d, 3H, J=6.6 Hz), 1.89 (m, 1H), 2.17 (s, 3H), 3.52 (dd, 1H, J=4.8, 9.0 Hz), 5.96 (dd, 1H, J=2.5, 4.6 Hz), 6.38 (br s, 1H), LRMS (negative ESI) 170 [(M−H)$^-$]. A suspension of this material (4.26 gm, 24.9 mmole) and K$_2$CO$_3$ (102 mg, 0.03 equiv) in MeOH (40 mL) was left stirring at RT for 1.5 hr. Amberlite IR-20 was then added to neutralize the reaction. This was filtered and the solvent was removed from the filtrate to leave crude (±)-cis-3-hydroxy-4-iso-propyl-azetidin-2-one. This material was dissolved in dry DMF (40 mL) and imidazole (3.39 gm, 2 equiv) and triethylsilyl chloride (4.19 mL, 1 equiv) were added. After 10 min, the reaction was partitioned between water and a mixture of EtOAc and hexane (1:1). The organic phase was washed with water (twice), brine and then dried (Na$_2$SO$_4$). The solvents were removed and the residue was chromatographed on a silica gel column (gradient elution with 25 to 35% EtOAc in hexane) to give (±)-cis-4-isopropyl-3-triethylsilyloxy-azetidin-2-one (4.63 gm, 77%): $^1$H NMR (CDCl$_3$) δ 0.65–1.03 (m, 21H), 1.93 (m, 1H), 3.29 (dd, 1H, J=4.8, 9.1 Hz), 4.87 (dd, 1H, J=2.8, 4.7 Hz), 6.05 (br s, 1H). A solution of this azetidinone (1.05 gm, 4.32 mmole), diisopropylethyl amine (0.90 mL, 1.2 equiv), di-tert-butyl dicarbonate (1.04 gm, 1.1 equiv) and p-dimethylamino pyridine (106 mg, 0.2 equiv) in dry DCM (10 mL) was left stirring at RT for 30 min. The reaction was diluted with DCM, washed with brine and dried (Na$_2$SO$_4$). Removal of the solvent followed by silica gel column chromatography (gradient elution with 10 to 20% EtOAc in hexane) afforded 1.31 gm (88%) of the title compound as an oil: $^1$H NMR δ (CDCl$_3$) 0.66–1.07 (m, 21H), 1.53 (s, 9H), 2.15 (m, 1H), 3.87 (t, 1H, J=6.4 Hz), 4.88 (d, 1H, J=6.1 Hz); LRMS (ESI) 344 [(M+H)]$^{+.}$ Preparation 3

(±)-cis-1-Benzoyl-4-isopropyl-3-triethylsilyloxy-azetidin-2-one

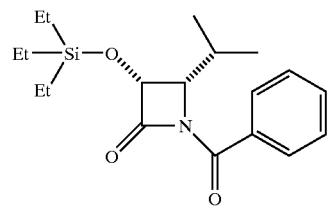

A solution of (±)-cis-4-isopropyl-3-triethylsilyloxy-azetidin-2-one (486 mg, 2.00 mmole), benzoyl chloride (0.255 mL, 1.1 equiv), diisopropylethyl amine (0.346 mL, 1.2 equiv) and p-dimethylaminopyridine (244 mg, 1 equiv) in dry DCM (6 mL) was left stirring at 0° C. for 6 hr. The bath was removed and the reaction was left stirring overnight. It was then diluted with DCM and washed with water, aq. HCl solution (0.1 N), saturated aq. NaHCO$_3$ solution, brine and dried (Na$_2$SO$_4$). Removal of the solvent followed by silica gel column chromatography (gradient elution with 0 to 5% EtOAc in hexane) gave the title compound: $^1$H NMR δ (CDCl$_3$) 0.47–0.94 (m, 21H), 2.09 (m, 1H), 4.07 (m, 1H), 4.75 (m, 1H), 7.24–7.76 (m, 5H).

Preparation 4
(3R,4R)-1-Neopentylcarbonyl-4-phenyl-3-triethylsilyloxy-azetidin-2-one

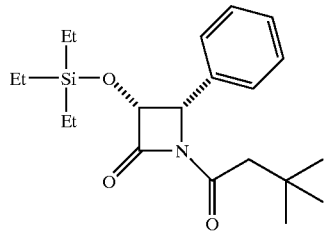

By following the above procedure and using neopentylcarbonyl chloride, and (3R,4R)-4-phenyl-3-triethylsilyloxy-azetidin-2-one were converted to the title product: $^1$H NMR (CDCl$_3$) δ 0.19–0.62 (m, 15H), 0.88 (s, 3H), 2.43 (d, 1H, J=13.8 Hz), 2.62 (d, 1H, J=14.1 Hz), 4.90 (d, 1H, J=5.7 Hz), 4.95 (d, 1H, J=6.0 Hz), 7.05–7.17 (m, 5H).

Preparation 5
(3R,4R)-1-Cyclobutylcarbonyl-4-phenyl-3-triethylsilyloxy-azetidin-2-one

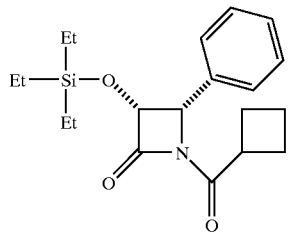

By following the above procedure and using cyclobutylcarbonyl chloride, (3R,4R)-4-phenyl-3-triethylsilyloxy-azetidin-2-one was converted to the title product: $^1$H NMR (CDCl$_3$) δ 0.18–0.61 (m, 15H), 1.66–2.22 (m, 6H), 3.61 (m, 1H), 4.89 (d, 1H, J=5.7 Hz), 4.94 (d, 1H, J=5.7 Hz), 7.03–7.18 (m, 5H).

Preparation 6
(3R,4R)-1-Neopentyloxycarbonyl-4-phenyl-3-triethylsilyloxy-azetidin-2-one

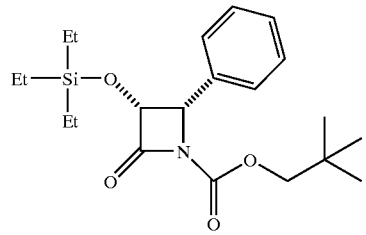

By following the above procedure and using neopentylchloroformate, (3R,4R)-4-phenyl-3-triethylsilyloxy-azetidin-2-one was converted to the title product: $^1$H NMR (CDCl$_3$) δ 0.39–0.97 (m, 24H), 3.73 (d, 1H, J=10.2 Hz), 3.90 (d, 1H, J=10.2 Hz), 5.10 (m, 2H), 7.31 (m, 5H).

Preparation 7

1) Synthesis of Baccatin Derivative 1

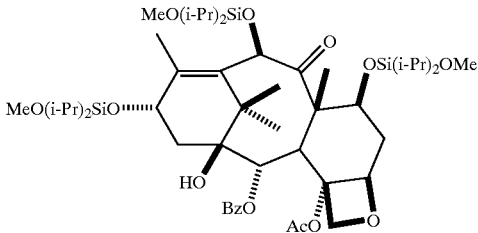

To a solution of 10-desacetylbaccatin (47.4 g, 87 mmol) in anhydrous N,N-dimethylformamide (DMF) (500 mL) was added imidazole (47 g, 691 mmol) at ambient temperature. Solution was stirred for 10–15 min until a clear solution was observed. Dropwise, diisopropyldichlorosilane (58 mL, 322 mmol) was added to the reaction mixture. Reaction mixture was stirred for 16 h at ambient temperature. Additional amount of diisopropyldichlorosilane (6 mL) was added to the solution and the reaction was stirred for 60 min. HPLC at this point indicated completion of the reaction. Methanol (36 mL) was added to the mixture and the solution was stirred for 60 min. Reaction was stopped and diluted with a mixture of tert-butyl methyl ketone (TBME) (500 mL) and water (200 mL). Layers were separated and organic phase was washed with brine (250 mL), dried (sodium sulfate) and evaporated to afford the trisilylated baccatin derivative 1, (91 g, >100% yield) as a white amorphous compound which was used in the next step without further purification.

ESILRMS M+ calcd. For C$_{50}$H$_{84}$O$_{13}$Si$_3$: 977. Found 977

2) Synthesis of Baccatin Derivative 2

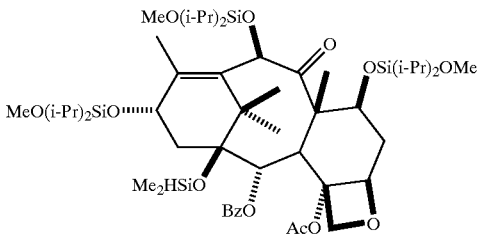

To a solution of baccatin derivative 1 (90 g, 92 mmol) in DMF (500 mL) was added imidazole (22 g, 320 mmol) at 0° C. Dimethylchlorosilane (35 mL, 320 mmol) was added dropwise at 0° C. Precipitation of the compound was observed at this point. Reaction mixture (slurry) was stirred for 0.5 h at 0° C. Solid was filtered and washed with cold DMF (3×150 mL). After air drying, solid was redissolved in TBME (700 mL) and the solution was washed with water (3×200 mL), brine (250 mL) and dried (sodium sulfate). The solution was filtered through a short silica pad. Removal of the solvent under vacuum afforded 2 in 77% yield (70 g).

ESILRMS M+ calcd. For C$_{50}$H$_{90}$O$_{13}$Si$_4$: 1035. Found 1035

3) Synthesis of Baccatin Derivative 3

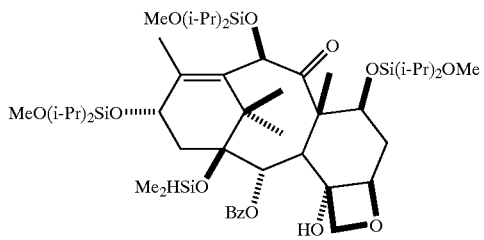

To a stirred solution of 2 (66.3 g, 64 mmol) in toluene (680 mL) at −34° C. was added Red-Al (50 mL, 160 mmol, 65 wt % solution of sodium bis(2-methoxyethoxy)aluminum hydride in toluene) dropwise over a period of 10 min. Reaction mixture was warmed to −25° C. and stirred for 1.5 h. Methanol (62 mL) was added dropwise to the reaction mixture keeping internal temperature between −20 and −25° C. Solution was diluted with TBME (500 mL) followed by the addition of 1N sodium hydroxide solution (60 mL) and brine (60 mL). Solution was stirred for 30 min. Celite (12 g) was added to the mixture, stirred for 10 min, and filtered through a pad of celite. Layers were separated. Organic layer was washed with water, brine, and dried (sodium sulfate). Next, solution was passed through a short silica pad before removal of the solvent. The compound was obtained in 97% yield (62 g) as a white solid.

ESILRMS M+ calcd. For $C_{50}H_{88}O_{12}Si_4$: 993. Found 993

4) Synthesis of Baccatin Derivative 4

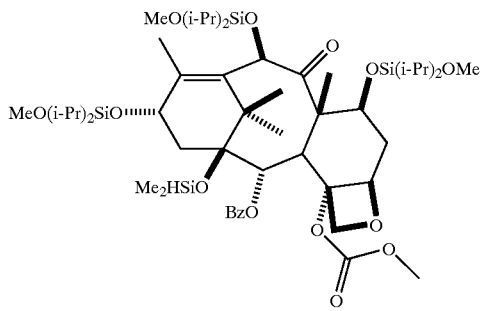

Under argon atmosphere, to a solution of 3 (62 g, 62 mmol) in anhydrous tetrahydrofuran (THF) (600 mL) at −60° C. was added LHMDS (lithium bis(trimethylsilyl) amide (125 mL, 125 mmol, 1M solution in THF) dropwise. Solution was stirred for 15 min followed by the addition of methyl chloroformate (9 mL, 116 mmol); internal temperature of the solution was maintained at −60° C. Reaction was slowly warmed to 0° C. and mixture was stirred for 3 h. After completion of the reaction, saturated ammonium chloride (300 L) was added. Reaction mixture was extracted with TBME (100 mL). Organic layer was washed with saturated ammonium chloride (200 mL), water (200 mL), brine (200 mL), dried (sodium sulfate), and evaporated to provide 4 as an oil (67 g, >100%). The crude material was used in the next step without further purification.

ESILRMS M+ calcd. For $C_{52}H_{90}O_{14}Si_4$: 1051. Found 1051.

5) Synthesis of Baccatin Derivative 5

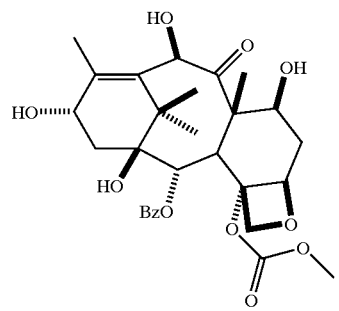

To a solution of baccatin derivative 4 (62 g, 59 mmol) in dry THF (260 mL) was added triethylamine.hydrofluoric acid complex (56 mL, 344 mmol) at ambient temperature. Reaction was stirred for 3 h. Reaction mixture was diluted with ethyl acetate (350 mL) and washed with water (200 mL), brine (200 mL), dried (sodium sulfate), and evaporated to afford 5 (43 g, >100% crude yield). Resluring of the crude compound in a mixture of hot ethylm acetate (350 mL) and hexanes (50 mL) gave pure 5 in 90% yield.

ESILRMS M+ calcd. For $C_{29}H_{36}O_{11}$: 560. Found 560.

6) Synthesis of Baccatin Derivative 6

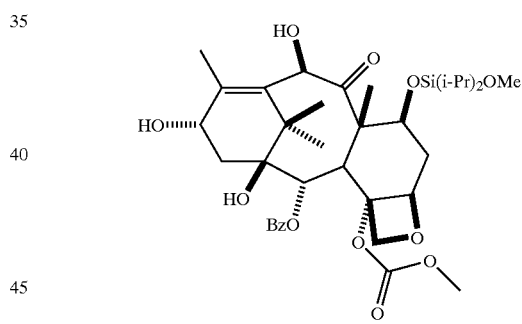

To a stirred solution of baccatin 5 (32 g, 57 mmol) and imidazole (11.7, 172 mmol in DMF (220 mL) at −65° C. was added diisopropyldichlorosilane (26.8 mL) under argon. Temperature of the reaction mixture was maintained at −60° C. and the mixture was stirred for 2 h. After completion of the reaction (HPLC), a solution of imidazole in methanol (11.7 g imidazole dissolved in 35 mL methanol) was added and the solution was stirred at 0° C. for 30 min. Mixture was extracted with TBME (500 mL). Organic phase was washed with water (4×150 mL), dried (sodium sulfate), and evaporated to afford crude 6 (45 g). The crude material was further dissolved in acetonitrile (150 mL) and the solution was washed with hexanes (3×100 mL). Removal of acetonitrile afforded pure 6 as a white solid (34 g, 84% yield).

ESILRMS M+ calcd. For $C_{36}H_{52}O_{12}Si$: 704. Found 704.

7) Synthesis of baccatin derivative 7 4-deacetyl-7-[bisisopropyl(methoxy)]silyloxy-4-methoxycarbonyl-baccatin

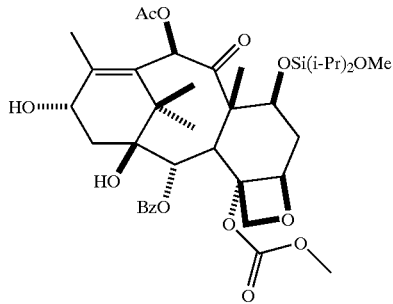

To a solution of baccatin derivative 6 (33.2 g, 47 mmol) in DMF (200 mL) was added LHMDS (61.2 mL, 61.2 mmol) dropwise at −43° C. Reaction was stirred for 15 min followed by the addition of acetic anhydride (5.8 mL, 63 mmol). Reaction was stirred for 30 min. at −40° C. Acetic acid (3.6 mL) was added and the cooling bath was removed. Reaction mixture was extracted with TBME (300 mL). Organic layer was separated and washed with water (3×150 mL), brine (150 mL), dried (sodium sulfate), and evaporated to afford the crude product. Purification of this compound was achieved by crystallization from a mixture of THF:heptane (1:6). Input of 40 g provided 21 g of crystallized baccatin derivative 7 (60% yield).

ESILRMS M+ calcd. For $C_{38}H_{54}O_{13}Si$: 746. Found 746.

EXAMPLE 1 COMPOUND Ia

3'-tert-Butyl-3'-N-tert-butyloxycarbonyl-4-deacetyl-3'-dephenyl-3'-N-debenzoyl-4-O-methoxycarbonyl-paclitaxel

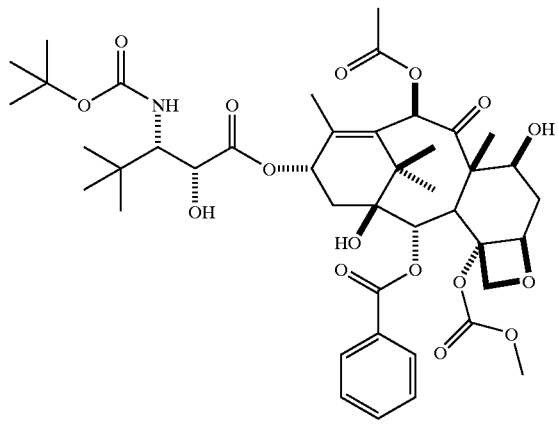

A solution of (±)-cis-4-tert-butyl-1-(tert-butyloxycarbonyl)-3-triethylsilyloxyazetidin-2-one (2.71 gm, 5 equiv) and 4-deacetyl-7-[bisisopropyl(methoxy)]silyloxy-4-methoxycarbonyl-baccatin (1.13 gm, 1.52 mmole) in dry THF (100 mL) under $N_2$ was cooled to −50° C. and a solution of LiHMDSA (1.97 mL, 1.3 equiv, 1.0 M in THF) was added. After 5 min this was transferred to a bath that was maintained at −35 to −30° C. for 20 hr and then −25° C. for 24 hr. The reaction was then quenched with saturated aqueous $NH_4Cl$ solution and extracted with a mixture of EtOAc and hexane (1:1). The organic extracts were washed with brine and dried ($Na_2SO_4$). The solvents were removed and the residue was chromatographed (radial chromatography on a 6 mm silica gel plate; gradient elution with 5 to 20% EtOAc in hexane) to afford 1.55 gm of 3'-tert-butyl-3'-N-tert-butyloxycarbonyl-7-[bisisopropyl (methoxy)]silyloxy-4-deacetyl-3'-dephenyl-3'-N-debenzoyl-4-O-methoxycarbonyl-2'-triethylsilyloxy paclitaxel as a mixture of 2',3'-diastereomers. This mixture was dissolved in dry THF (60 mL) and triethylamine trihydrofluoride (0.92 mL 4 equiv) were added. After 22 hr at RT, the reaction was neutralized with saturated aq. NaHCO3 solution and then extracted with EtOAc. The organic extracts were washed with brine, dried ($Na_2SO_4$) and the solvents were removed. The residue was chromatographed (radial chromatography; 2 mm silica gel plate; gradient elution from 10 to 50% EtOAc in hexane) to afford (in order of elution): 210 mg (18%) of 2'S,3'R-3'-tert-butyl-3-'N-tert-butyloxycarbonyl-4-deacetyl-3'-dephenyl-3'-N-debenzoyl-4-O-methoxycarbonyl-paclitaxel {$^1$H NMR ($CDCl_3$) δ 1.04 (s, 9H), 1.13 (s, 3H), 1.20 (s, 3H), 1.37 (s, 9H), 1.65 (s, 1H), 1.66 (s, 3H), 1.84–1.93 (m, 2H), 2.17 (s, 3H), 2.25 (s, 3H), 2.55 (m, 3H), 3.00 (d, 1H, J=6.5 Hz), 3.74 (d, 1H, J=10.8 Hz), 3.79 (d, 1H, J=6.9 Hz), 3.92 (s, 3H), 4.16 (d, 1H, J=8.5 Hz), 4.33 (d, 1H, J=8.5 Hz), 4.42 (m, 1H), 4.54 (d, 1H, J=6.5 Hz) 4.87 (d, 1H, J=10.6 Hz), 5.01 (d, 1H, J=7.7 Hz), 5.68 (d, 1H, J=7.0 Hz), 5.76 (m, 1H), 6.32 (s, 1H), 7.44–8.05 (m, 5H); LRMS (ESI) 846 [(M+H)$^+$]} and 668 mg (56%) of the title compound {$^1$H NMR ($CDCl_3$) δ 1.07 (s, 9H), 1.14 (s, 3H), 1.24 (s, 3H), 1.33 (s, 9H), 1.66 (s, 4H), 2.23 (s, 3H), 2.38–2.59 (m, 4H), 3.11 (d, 1H, J=5.8 Hz), 3.77 (d, 1H, J=11.1 Hz), 3.82 (d, 1H, J=7.0 Hz), 3.96 (s, 3H), 4.20 (d, 1H, J=8.6 Hz), 4.33 (d, 1H, J=8.6 Hz), 4.39 (m, 1H), 4.53 (d, 1H, J=5.4 Hz) 4.88 (d, 1H, J=10.6 Hz), 4.98 (d, 1H, J=7.9 Hz), 5.69 (d, 1H, J=7.1 Hz), 6.03 (m, 1H), 6.28 (s, 1H), 7.40–8.11 (m, 5H); LRMS (ESI) 846 [(M+H)$^+$]}.

EXAMPLE 2 COMPOUND Ib

3'-N-tert-Butyloxycarbonyl-4-deacetyl-3'-dephenyl-3'-N-debenzoyl-3'-isopropyl-4-O-methoxycarbonyl-paclitaxel By following the above procedure, (±)-cis-1-tert-butyloxycarbonyl-4-isopropyl-3-triethylsilyloxy-azetidin-2-one was coupled with 4-deacetyl-7-[bisisopropyl(methoxy)] silyloxy-4-O-methoxycarbonyl-baccatin. Deprotection followed by chromatography gave the title compound $^1$H NMR ($CDCl_3$+$D_2O$) δ 1.03 (d, 3H, J=6.7 Hz), 1.09 (d, 3H, J=6.7 Hz), 1.14 (s, 3H), 1.24 (s, 3H), 1.31 (s, 9H), 1.66 (m, 3H), 1.83–2.02 (m, 5H), 2.24 (s, 3H), 2.25–2.59 (m, 3H), 3.68 (dd, 1H, J=2.0, 9.2 Hz), 3.82 (d, 1H, J=6.9 Hz), 3.98 (s, 3H), 4.19 (d, 1H, J=8.6 Hz), 4.34 (d, 1H, J=8.6 Hz), 4.39 (m, 1H), 4.43 (d, 1H, J=2.0 Hz) 4.82 (br s, 1H), 4.98 (d, 1H, J=7.8 Hz), 5.69 (d, 1H, J=7.0 Hz), 6.11 (m, 1H), 6.28 (s, 1H), 7.45–8.12 (m, 5H); LRMS (ESI) 832 [(M+H)$^+$].

EXAMPLE 3 COMPOUND Ic

3'-N-Neopentylcarbonyl-4-deacetyl-3'-N-debenzoyl-4-O-methoxycarbonyl-paclitaxel

A solution of (3R,4R)-1-neopentylcarbonyl-4-phenyl-3-triethylsilyloxy-azetidin-2-one (525 mg, 1.4 equiv) and 4-deacetyl-7-[bisisopropyl(methoxy)]silyloxy-4-O-methoxycarbonyl-baccatin (523 mg, 0.700 mmole) in dry THF (15 mL) was cooled to −50° C. and a solution of LiHMDSA (0.84 mL, 1.2 equiv, 1.0 M in THF) was added with stirring. After 40 min, the reaction was allowed to warm to 0° C. After 1.5 hr, this was quenched with a saturated aq. solution of $NH_4Cl$, the reaction was extracted with EtOAc. The organic extract was washed with a saturated aq. solution of $NH_4Cl$, water, brine and dried ($Na_2SO_4$). Removal of the solvents followed by silica gel column chromatography (gradient elution with mixtures of 0% to 20% EtOAc in hexane) afforded 2.78 mg (54%) of 3'-N-neopentyloxycarbonyl-7-[bisisopropyl(methoxy)]silyloxy-4-deacetyl-3'-N-debenzoyl-4-O-methoxycarbonyl-2'-triethylsilyloxy-paclitaxel. This was taken directly and treated with triethylamine trihydrofluoride (0.161 mL, 4 equiv) in dry THF (6 mL) and left stirring at RT overnight. After neutralization with saturated aq. NaHCO$_3$ solution, the reaction was extracted with EtOAc. The organic extracts were washed with brine and dried (Na$_2$SO$_4$). Removal of the solvents followed by silica gel column chromatography (gradient elution with mixtures of 20 to 50% EtOAc in hexane) afforded 151 mg (71%) of the title product: $^1$H NMR (CDCl$_3$) δ 0.96–2.58 [32H, including 0.96 (s, 9H), 1.14 (s, 3H), 1.24 (s, 3H), 1.66 (s, 3H), 1.84 (s, 3H), 2.23 (s, 3H)], 3.58 (br s, 1H), 3.77 (s, 3H), 3.80 (d, 1H, J=5.5 Hz), 4.19 (d, 1H, J=8.3 Hz), 4.33 (d, 1H, J=8.7 Hz), 4.36 (m, 1H), 4.65 (d, 1H, J=2.0 Hz), 4.95 (d, 1H, J=8.5 Hz), 5.58 (dd, 1H, J=2.3, 8.8 Hz), 5.69 (d, 1H, J=7.0 Hz), 6.11 (d, 1H, J=8.9 Hz), 6.16 (m, 1H), 6.27 (s, 1H), 7.29–8.12 (m, 10H); LRMS (ESI) 864 [(M+H)$^+$].

EXAMPLE 4 COMPOUND Id

3'-N-Cyclobutyl-4-deacetyl-3'-N-debenzoyl-4-O-methoxycarbonyl-paclitaxel

By following the above procedure and using (3R,4R)-1-cyclobutyl-4-phenyl-3-triethylsilyloxy-azetidin-2-one, 4-deacetyl-7-[bisisopropyl(methoxy)]silyloxy-4-O-methoxycarbonyl-baccatin was converted to the title product: $^1$H NMR (CDCl$_3$) δ 1.14–2.53 [m, 27H including: 1.14 (s, 3H), 1.25 (s, 3H), 1.67 (s, 3H), 1.84 (s, 3H), 2.24 (s, 3H)], 3.01 (m, 1H), 3.56 (br s, 1H), 3.81 (s, 3H), 3.82 (m, 1H), 4.20 (d, 1H, J=8.4 Hz), 4.34 (d, 1H, J=8.5 Hz), 4.37 (m, 1H), 4.68 (d, 1H, J=2.3 Hz), 4.96 (d, 1H, J=8.6 Hz), 5.58 (dd, 1H, J=2.4, 9.0 Hz), 5.70 (d, 1H, J=7.0 Hz), 6.16 (m, 2H), 6.27 (s, 1H), 7.29–8.14 (m, 10H); LRMS (ESI) 848 [(M+H)$^+$].

EXAMPLE 5 COMPOUND Ie

3'-tert-Butyl-3'-N-cyclohexyloxycarbonyl-4-deacetyl-3'-dephenyl-3'-N-debenzoyl-4-O-methoxycarbonyl-paclitaxel By following the same procedure with cyclohexyloxychloroformate, 3'-tert-butyl-3-'N-tert-butyloxycarbonyl-4-deacetyl-3'-dephenyl-3'-N-debenzoyl-4-O-methoxycarbonyl-paclitaxel was converted to the title product: $^1$H NMR (CDCl$_3$+D$_2$O) δ 1.10–2.61 [38H, including 1.10 (s, 9H), 1.16 (s, 3H), 1.26 (s, 3H), 1.69 (s, 3H), 1.95 (s, 3H), 2.26 (s, 3H)], 3.84 (m, 2H), 3.99 (s, 3H), 4.23 (d, 1H, J=8.6 Hz), 4.40 (m, 3H), 4.57 (s, 1H), 5.02 (m, 2H), 5.7 (d, 1H, J=7.08 Hz), 6.06 (m, 1H), 6.30 (s, 1H), 7.46–8.13 (m, 5H); LRMS (ESI) 872 [(M+H)$^+$].

EXAMPLE 6 COMPOUND If

3'-tert-Butyl-4-deacetyl-3'-dephenyl-3'-N-debenzoyl-3'-N-neopentylcarbonyl-4-O-methoxycarbonyl-paclitaxel By following the above procedure with tert-butylacetyl chloride, 3'-tert-butyl-3-N-tert-butyloxycarbonyl-4-deacetyl-3'-dephenyl-3'-N-debenzoyl-4-O-methoxycarbonyl-paclitaxel was converted to the title product $^1$H NMR (CDCl$_3$+D$_2$O) δ 1.00–2.56 [39H, including 1.00 (s, 9H), 1.11 (s, 9H), 1.16 (s, 3H), 1.26 (s, 3H), 1.69 (s, 3H), 1.91 (s, 3H), 2.26 (s, 3H)], 3.83 (d, 1H, J=7.1 Hz), 3.98 (s, 3H), 4.17 (d, 1H, J=10.1 Hz), 4.26 (d, 1H, J=8.8 Hz), 4.37 (m, 2H), 4.55 (s, 1H), 5.00 (d, 1H, J=7.5 Hz), 5.73 (m, 2H), 6.02 (m, 1H), 6.29 (s, 1H), 7.45–8.13 (m, 5H); LRMS (ESI) 844 [(M+H)$^+$].

EXAMPLE 7 COMPOUND Ig 4-deacetyl-3'-N-debenzoyl-3'-N-tertbutoxycarbonyl-4-O-methoxycarbonyl-paclitaxel By following the above procedures and using (3R,4R)-1-tertbutoxycarbonyl-4-phenyl-3-triethylsilyloxy-azetidin-2-one, compound Ig was prepared.

1H NMR (300 MHz, CDCl$_3$): δ 8.13–8.10 (m, 2H), 7.61–7.26 (m, 8H), 6.27 (s, 1H), 6.19 (m, 1H), 5.68 (d, J=6.9 Hz, 1H), 5.35–5.29 (m, 2H), 4.97 (d, J=7.7 Hz, 1H), 4.63 (d, J=3.9 Hz, 1H), 4.42–4.37 (m, 1H), 4.25 (AB q, J=8.8 Hz, J=47.7 Hz, 2H), 3.85–3.81 (m, 4H), 3.40 (d, J=5.1 Hz, 1H), 2.59–1.03 (m, 30H, include singlets at 2.24, 1.87, 1.71, 1.27, 1.14, 3H each, 1.32, 9H).

EXAMPLE 8 COMPOUND Ih 4-deacetyl-3'-N-debenzoyl-3'-N-nbutoxycarbonyl-4-O-methoxycarbonyl-paclitaxel Using the procedures described above with (3R,4R)-1-nbutoxycarbonyl-4-phenyl-3-triethylsilyloxy-azetidin-2-one, compound Ih was prepared.

1H NMR (300 MHz, CDCl$_3$): δ 8.11 (d, J=7.4 Hz, 2H), 7.62–7.29 (m, 10H), 6.27 (s, 1H), 6.27 (m, 1H), 5.69 (d, J=7.0 Hz, 1H), 5.41 (abq, J=47.4, 9.4 Hz, 2H), 4.97 (d, J=7.0 Hz, 1H), 4.66 (brs, 1H), 4.38–4.32 (m, 1H), 4.26 (abq, 45.0, 8.6 Hz, 2H), 3.83 (s, 3H), 3.42 (brd, J=4.1 Hz, 1H), 2.59–2.35 (m, 4H), 2.24 (m, 3H), 1.86 (s, 3H), 1.67 (s, 3H), 1.65 (d, J=33.0 Hz, 3H), 1.67 (s, 3H), 1.51–1.47 (m, 2H), 1.24 (s, 3H), 1.14 (s, 3H), 0.83 (m, 3H).

Anal. calcd. for C$_{45}$H$_{55}$NO$_{16}$: C, 62.42; H, 6.40; N, 1.62. Found: C, 62.28; H, 6.45; N, 1.55.

EXAMPLE 9 COMPOUND Ii

3'-N-debenzoyl-3'-N-cyclobutylcarbonyl-3'-dephenyl-3'-tert-butyl-4-deacetyl-4-methoxycarbonyl paclitaxel A solution of 3'-N-debenzoyl-3'-N-tert-butyl-3'-dephenyl-3'-tert-butyl-4-deacetyl-4-methoxycarbonyl paclitaxel (2.30 g, 2.72 mmoles) in DCM (15.0 mL) was treated with trifluoroacetic acid (15.0 mL) and stirred at stirred at 0° C. for 1.5 hrs. The mixture was diluted with 100 mL DCM and poured into a cold solution (0° C.) made up of 50.0 g NaHCO$_3$ in 150 mL water. The phases were separated and the organic layer was concentrated in vacuo. The product could be purified by column chromatography on silica gel eluting with 4% methanol/DCM, but was generally used without purification. The crude 3'-N-debenzoyl-3'-dephenyl-3'-tert-butyl-4-deacetyl-4-methoxycarbonyl paclitaxel was dissolved in ethyl acetate (15.0 mL) and treated with saturated NaHCO$_3$ (15.0 mL). Cyclobutane carbonyl chloride (460.0 μL, 4.08 mmoles, 1.5 equiv.) was added and the biphasic mixture was stirred vigorously at ambient temperature for 20 mins. The mixture was diluted with ethyl acetate, and the phases were separated. The organic phase was washed with saturated NaHCO$_3$, then brine. The organic solution was dried over anhydrous Na$_2$SO$_4$, filtered and concentrated in vacuo. Purification by preparative reverse phase chromatography eluting with 20% acetonitrile/water for 5 mins. ramping up to 60% acetonitrile/water over 45 mins, then isocratic for 45 mins. at a flow rate of 250 mL/min. afforded the title compound (1.47 g, 65% yield, 97% pure by HPLC analysis) as a white, amorphous solid which exhibited the following physical properties: $^1$H NMR (CDCl$_3$, 300 MHz) δ 8.08 (d, J=7.1 Hz, 2H), 7.62–7.55 (m, 1H), 7.48–7.43 (m, 2H), 6.27 (s, 1H), 5.99 (dd, J=7.8 Hz, J=9.0 Hz, 1H), 5.69 (m, 2H), 4.98 (dd, J=2.0 Hz, J=9.5 Hz, 1H), 4.55 (dd, J=1.1 Hz, J=5.2 Hz, 1H), 4.40–4.32 (bm, 2H), 4.22 (d, J=8.4 Hz, 1H), 4.14 (d, J=10.2 Hz, 1H), 3.98 (s, 3H), 3.80 (d, J=7.0 Hz, 1H), 3.30 (d, J=5.1 Hz, 1H), 2.97 (p, J=7.9 Hz, 1H), 2.58–2.36 (bm, 4H), 2.23 (s, 3H), 2.19–2.03 (bm, 4H), 1.92–1.76 (bm, 3H), 1.88 (s, 3H), 1.66 (s, 3H), 1.24 (s, 3H), 1.14 (s, 3H), 1.06 (s, 9H); $^{13}$C NMR (CDCl$_3$, 75 MHz) δ 203.70, 174.99, 174.93, 171.46, 166.89, 153.21, 142.54, 133.74, 133.20, 130.22, 129.81, 128.72, 84.13, 83.21, 78.92, 76.09, 75.68, 74.94, 73.39, 72.06, 70.17, 58.36, 57.73, 56.03, 51.07, 45.74, 43.34, 39.91, 35.94, 35.47, 27.37, 26.85, 25.60, 25.44, 22.12, 20.95, 18.29, 14.95, 9.72; LRMS (ESI): 828.51 ((M+1)$^+$, 100%), 886.57 ((M+NH$_4$+ACN)$^+$, 15%); 826.48 ((M−1)$^−$, 100%).

EXAMPLE 10 COMPOUND Ik

3'-N-debenzoyl-3'-N-(2-furoyl)-3'-dephenyl-3'-tert-butyl-4-deacetyl-4-methoxycarbonyl paclitaxel Prepared similarly to Example 9 above. The title compound (2.13 g, 73% yield, 98% pure by HPLC analysis) was obtained as a white, amorphous solid which exhibited the following physical properties: $^1$H NMR (CDCl$_3$, 300 MHz) δ 8.15–8.08 (m, 2H), 7.64–7.56 (m, 1H), 7.52–7.25 (m, 3H), 7.03 (dd, J=0.6 Hz, J=3.4 Hz, 1H), 6.78 (d, J=10.2 Hz, 1H), 6.48 (dd, J=1.8 Hz, J=3.5 Hz, 1H), 6.25 (s, 1H), 6.06 (dd, J=7.6 Hz, J=8.9 Hz, 1H), 5.70 (d, J=7.0 Hz, 1H), 5.00 (dd, J=1.9 Hz, J=9.4 Hz, 1H), 4.40–4.32 (m, 3H), 4.23 (d, J=8.6 Hz, 1H), 4.05 (s, 3H), 3.48 (d, J=4.5 Hz, 1H), 2.60–2.50 (m, 2H), 2.38 (dd, J=3.3 Hz, J=8.8 Hz, 1H), 2.23 (s, 3H), 2.05 (s, 1H), 1.95–1.85 (m, 1H), 1.81 (s, 3H), 1.68 (s, 3H), 1.21 (s, 3H), 1.14 (s, 12H); $^{13}$C NMR (CDCl$_3$, 75 MHz) δ 203.71, 174.23, 171.55, 167.06, 158.22, 153.06, 147.65, 144.30, 142.53, 133.93, 133.36, 130.32, 129.42, 128.88, 114.95, 112.51, 84.20, 83.48, 79.06, 77.65, 76.20, 75.81, 75.05, 72.96, 70.55, 58.50, 57.97, 56.40, 46.07, 43.33, 36.09, 35.55, 27.53, 27.05, 22.00, 21.25, 21.06, 14.97, 14.39, 9.83; LRMS (ESI): 840.43 ((M+1)$^+$, 100%); 838.43 ((M−1)$^−$, 100%).

Biological Data

Another aspect of the instant invention concerns a method for inhibiting human and/or other mammalian tumors which comprises orally administering to a tumor bearing host an antitumor effective amount of a compound of formula I.

The materials and methods utilized for the in vivo antitumor testing of our oral taxanes are summarized below:

Materials

Animals. Conventional or athymic ("nude") mice, and nude rats, were implanted subcutaneously (sc) with tumor brei or fragments. Murine tumor were implanted in conventional mice, human tumors were implanted into nude mice or rats.

Tumors. The tumors utilized most often included the murine lung carcinoma, M109, the murine mammary carcinoma, MAM 16/C, the human ovarian carcinoma, A2780, the human colon tumors, HCT-116 and HCT-116/pk. Compounds I exhibited antitumor activity after oral administration in one or more of the aforementioned tumor models.

Methods for the Table III Results

The experiments were carried out using athymic ("nude") mice. Typically, treatments were begun when tumors were between 100 and 500 mg in size (typically Day 7 to Day 12 post-tumor implant) for the A2780 human ovarian tumor xenograft model. Group sizes were typically 8 per treatment and control groups in mouse experiments. The compound was administered at the dose indicated in Table III, namely, once daily every other day for five treatments (i.e. q2dx5).

Treatments for taxanes administered orally (po) were done by gavage using a vehicle consisting of 10% ethanol+ 10% Cremophor EL+80% water. The volume of liquid administered was 0.01 ml per gram of body weight for mice. A typical mouse experiment would involve the evaluation of each test compound at three different dose levels.

Antitumor activity was assessed by determining the size of tumors in all treated and control experimental animals over time. Each animal was individually identified and the growth of the tumor implanted into each animal was measured once or twice weekly using a calipers. The difference in median time for tumors in treated (T) and control (C) groups to reach a predetermined size (e.g., 500 or 1,000 milligrams) was calculated, and assessments of absolute and relative antitumor effects (e.g., between compounds) were made on the basis of the delays in time to reach predetermined tumor target sizes. Animals with tumors of 35 mg or less at the termination of an experiment were termed "cures". Experiments were terminated typically after a period of time had elapsed post-treatment that was at least 10 times the tumor volume doubling time (TVDT) of the median tumor growth in control animals as assessed prior to their reaching the predetermined tumor target size in each experiment. Activity in a test group was defined as having caused a delay in tumor growth (median time to reach tumor target size) relative to the concomitant control tumor growth (i.e., T-C) of 3.32 times the TVDT. Activity was expressed in "log cell kill" which was equal to (T-C)/(TVDT×3.32). Toxicity was determined by measuring the average body weight of all animals in an experiment prior to, and soon after, any treatments in the experiment. Additionally, animals were considered to have died due to treatment-induced injury if they died prior to any deaths in the control group with tumors smaller than target size. No results of therapy, nor any declaration of activity, was used or made for a particular treatment group if more than one animal in that group died in a manner characterized as treatment-induced.

All of the compounds in Table III displayed oral antitumor activity in a ScM109 tumor model implanted in mice which was judged to be equivalent to the antitumor activity of paclitaxel administered intravenously according to its optimum schedule of administration and dose.

TABLE III

In Vivo Activity vs Sc A2780 of Orally Active C-4 Methyl Carbonate Taxanes

| Compound | Oral Dose[a] | Schedule | Oral Efficacy vs. Sc A2780 Log Cell Kill[c] (Cures/Treated)[b] |
|---|---|---|---|
| Ia | 65 | q2dx5 | 4.4 (0/8) |
| Ib | 28 | q2dx5 | 3.0 (1/8)** |
| Ic | 100 | q2dx5 | 3.8 (0/8) |
| Id | 140 | q2dx5 | 4.1 (0/8) |
| Ie | 55 | q2dx5 | 1.5 (0/8) |
| If | 36 | q2dx5 | 1.8 (0/8) |
| Ig | 32 | q2dx5 | 0.9 (0/8) |
| Ih | 100 | q2dx5 | 7.0 (1/8)** |

TABLE III-continued

In Vivo Activity vs Sc A2780 of
Orally Active C-4 Methyl Carbonate Taxanes

| Compound | Oral Dose[a] | Schedule | Oral Efficacy vs. Sc A2780 Log Cell Kill[c] (Cures/Treated)[b] |
|---|---|---|---|
| Ij | 120 | q2dx5 | 2.1 (0/8) |
| Ik | 130 | q2dx5 | 2.2 (0/8) |

[a]Optimal or maximum tolerated dose level tested in milligrams per kilogram. The dose given is for a single administration and is repeated for each of the five administrations. The total amount of compound given for the complete course of treatment is therefore five times the oral dose indicated in Table III.
**One of eight tested mice was cured
[b]The number of mice judged to be cures (as defined above) divided by the total number of treated mice is the meaning for "cures/treated," which appears in parenthesis in Table III.
[c]"Log Cell Kill" has already been defined above.

As can be seen from the results of Table III, all the compounds Ia-Ik displayed significant oral antitumor activity. Significant antitumor activity is defined as being approximately one log cell kill. This can be contrasted with results that would be observed for compounds which would have no oral activity, such as paclitaxel (i.e. having approximately zero log cell kill). It should be recognized that paclitaxel, which is the active ingredient of the commercially available anticancer drug, TAXOL®, is administered intravenously and is not used in oral administration since it is not effective.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m2 over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. Additional examples of paclitaxel formulations are found in the general references cited earlier in the background art. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:
1. A process for preparing a compound of formula I,

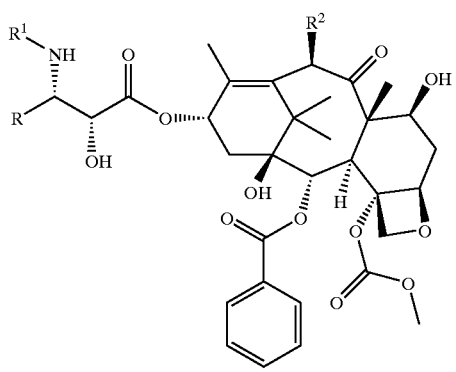

wherein:

R is phenyl, isopropyl, or tert butyl;
$R^1$ is —C(O)$R^z$ in which $R^z$ is (CH$_3$)$_3$CO—, (CH$_3$)$_3$CCH$_2$—, CH$_3$(CH$_2$)$_3$O—, cyclobutyl-, cyclohexyloxy, or (2-furyl); and
$R^2$ is CH$_3$C(O)O—, comprising the steps of:

(a) reacting a compound of formula II,

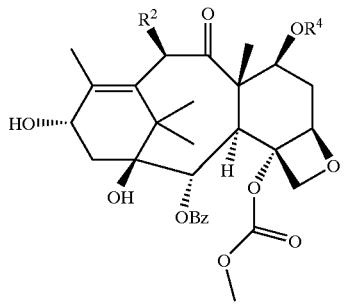

wherein $R^2$ is as defined hereinabove, and $R^4$ is a hydroxy protecting group, with a beta-lactam of formula IV,

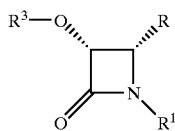

wherein $R^1$ and R are as defined hereinabove, and $R^3$ is a hydroxy protecting group, in presence of a base to produce the compound of formula III,

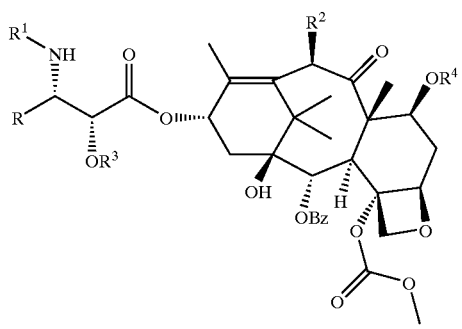

wherein R, $R^1$, $R^2$, $R^3$ and $R^4$ are as defined hereinabove; and (b) deprotecting the hydroxy protecting groups $R^3$ and $R^4$ of the compound of formula III to provide the compound of formula I.

2. The process of claim 1, wherein said hydroxy protecting group is selected from the group consisting of ether, dialkylsilylether, trialkylsilylether, dialkylalkoxysilylether, ester and carbonate.

3. The process of claim 2, wherein:

said ether hydroxy protecting group is methyl, t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, or tetrahydrothiopyranyl;

said dialkylsilylether hydroxy protecting group is dimethylsilyl;

said trialkylsilylether hydroxy protecting group is trimethylsilyl, triethylsilyl, or t-butyldimethylsilyl;

said dialkylalkoxysilylether hydroxy protecting group is diisopropyl methoxy silyl;

said ester hydroxy protecting group is benzoyl, acetyl, phenylacetyl, formyl, mono-, di-, or trihaloacetyl; and said canbonate hydroxy protecting group is methyl, ethyl, 2,2,2-trichloroethyl, allyl, benzyl or p-nitrophenyl.

4. The process of claim 1, wherein $R^3$ is selected from the group consisting of 1-methyl-1-methoxyethyl (MOP), trialkyl silyl and dialkyl alkoxy silyl; and $R^4$ is selected from the group consisting of dialkyl alkoxy silyl, trialkyl silyl and benzyl carbonate.

5. The process of claim 1, wherein $R^3$ is triethyl silyl or t-butyldimethylsilyl; and $R^4$ is diisopropyl methoxy silyl.

6. The process of claim 1, wherein said step (b) comprises contacting the compound of formula III with at least one compound selected from the group consisting of a fluoride source and an acid.

7. A process for preparing a compound of formula Ia,

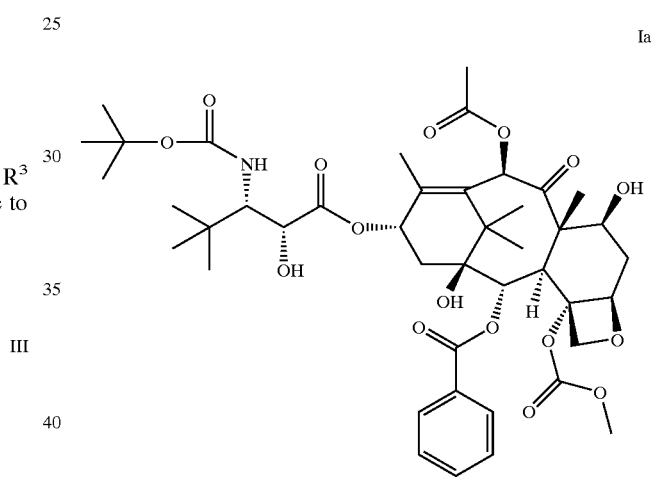

comprising the steps of:

(a) reacting a compound of formula IIa,

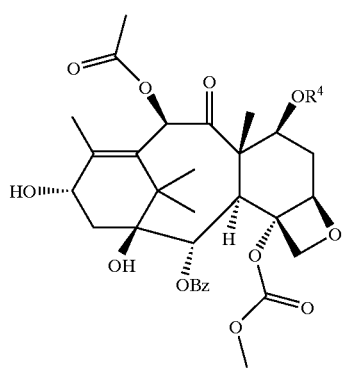

wherein $R^4$ is a hydroxy protecting group, with a beta-lactam of formula IVa,

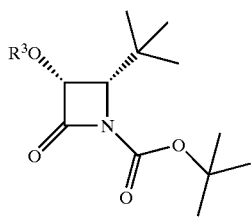

wherein $R^3$ is a hydroxy protecting group,
in the presence of a base to produce a compound of formula IIIa,

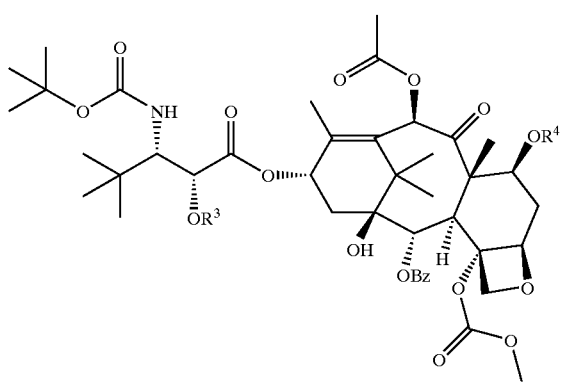

wherein $R^3$ and $R^4$ are as defined hereinabove; and (b) deprotecting the hydroxy protecting groups $R^3$ and $R^4$ of the compound of formula IIIa to provide a compound of formula Ia.

8. The process of claim 7, wherein said hydroxyl protecting group is selected from the group consisting of ether, dialkylsilylether, trialkylsilylether, dialkylalkoxysilylether, ester and carbonate.

9. The process of claim 8, wherein:
said ether hydroxyl protecting group is methyl, t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, or tetrahydrothiopyranyl;
said dialkylsilylether hydroxyl protecting group is dimethylsilyl;
said trialkylsilylether hydroxyl protecting group is trimethylsilyl, triethylsilyl, or t-butyldimethylsilyl;
said dialkylalkoxysilylether hydroxyl protecting group is diisopropyl methoxy silyl;
said ester hydroxyl protecting group is benzoyl, acetyl, phenylacetyl, formyl, mono-, di-, or trihaloacetyl; and
said canbonate hydroxyl protecting group is methyl, ethyl, 2,2,2-trichloroethyl, allyl, benzyl or p-nitrophenyl.

10. The process of claim 7, wherein $R^3$ is selected from the group consisting of 1-methyl-1-methoxyethyl (MOP), trialkyl silyl and dialkyl alkoxy silyl; and $R^4$ is selected from the group consisting of dialkyl alkoxy silyl, trialkyl silyl and benzyl carbonate.

11. The process of claim 7, wherein $R^3$ is triethyl silyl or t-butyldimethylsilyl; and $R^4$ is diisopropyl methoxy silyl.

12. The process of claim 7, wherein said step (b) comprises contacting the compound of formula III with at least one reagent selected from the group consisting of a fluoride source and an acid.

13. A process for preparing a compound of formula I,

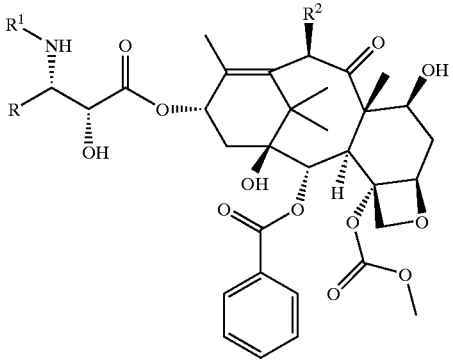

wherein:

R is phenyl, isopropyl, or tert butyl;
$R^1$ is $-C(O)R^Z$ in which $R^Z$ is $(CH_3)_3CO-$, $(CH_3)_3CCH_2-$, $CH_3(CH_2)_3O-$, cyclobutyl-, cyclohexyloxy, or (2-furyl); and
$R^2$ is $CH_3C(O)O-$, comprising the steps of:
(a) deprotecting a compound of formula V,

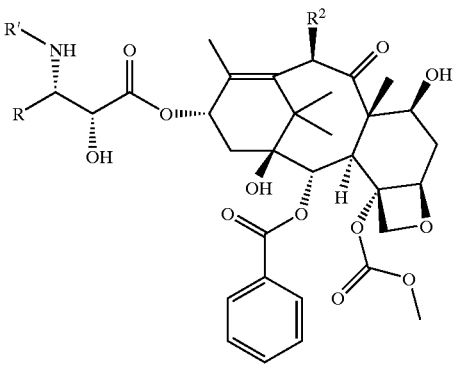

wherein R and $R^2$ are as defined hereinabove, and R' is an amine protecting group, to produce a compound of formula VI,

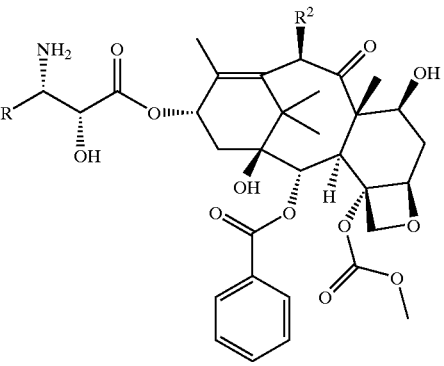

wherein R and $R^2$ are as defined hereinabove; and (c) attaching $R^1$ to the $NH_2$ group of the compound of VI by reacting the compound of formula VI with a compound containing $R^1$.

14. The process of claim 13, wherein said compound containing $R^1$ is selected from the group consisting of acid chloride, chloroformate and acid anhydride.

15. The process of claim 14, wherein R' is BOC or CBZ.

16. The process of claim 15, wherein R is tert butyl, and $R^1$ is —C(O)$R^Z$ in which $R^Z$ is $(CH_3)_3CO$—.

17. A compound of formula III,

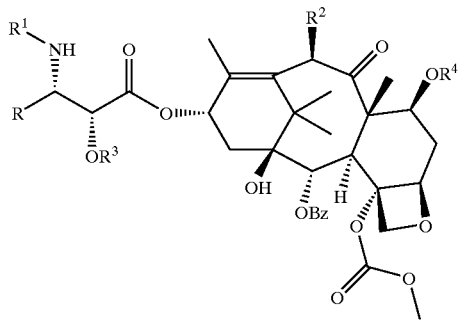

III wherein:

R is phenyl, isopropyl, or tert butyl;

$R^1$ is —C(O)$R^Z$ in which $R^Z$ is $(CH_3)_3CO$—, $(CH_3)_3CCH_2$—, $CH_3(CH_2)_3O$—, cyclobutyl-, cyclohexyloxy, or (2-furyl);

$R^2$ is $CH_3C(O)O$—; and $R^3$ and $R^4$ are each independently a hydroxy protecting group.

18. The compound of claim 17, wherein said hydroxy protecting group is selected from the group consisting of ether, dialkylsilylether, trialkylsilylether, dialkylalkoxysilylether, ester and carbonate.

19. The compound of claim 18, wherein:

said ether hydroxy protecting group is methyl, t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, or tetrahydrothiopyranyl;

said dialkylsilylether hydroxy protecting group is dimethylsilyl;

said trialkylsilylether hydroxy protecting group is trimethylsilyl, triethylsilyl, or t-butyldimethylsilyl;

said dialkylalkoxysilylether hydroxy protecting group is diisopropyl methoxy silyl;

said ester hydroxy protecting group is benzoyl, acetyl, phenylacetyl, formyl, mono-, di-, or trihaloacetyl; and said carbonate hydroxy protecting group is methyl, ethyl, 2,2,2-trichloroethyl, allyl, benzyl or p-nitrophenyl.

20. The compound of claim 17, wherein $R^3$ is selected from the group consisting of 1-methyl-1-methoxyethyl (MOP), trialkyl silyl and dialkyl alkoxy silyl; and $R^4$ is selected from the group consisting of dialkyl alkoxy silyl, trialkyl silyl and benzyl carbonate.

21. The compound of claim 17, wherein $R^3$ is triethyl silyl or t-butyldimethylsilyl; and $R^4$ is diisopropyl methoxy silyl.

22. The compound of claim 21, wherein R is tert butyl; and $R^1$ is —C(O)$R^Z$ in which $R^Z$ is $(CH_3)_3CO$—.

23. A compound of formula V,

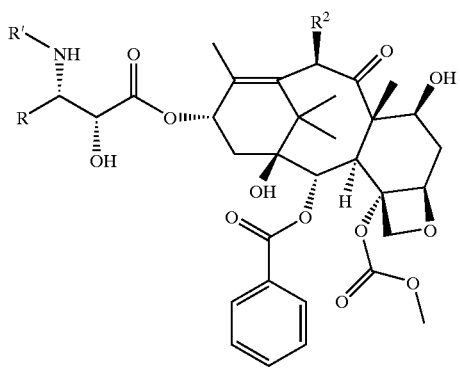

V wherein:

R is phenyl, isopropyl, or tert butyl;

R' is an amine protecting group; and $R^2$ is $CH_3C(O)O$—.

24. The compound of claim 23, wherein R is tert butyl.

25. The compound of claim 24, wherein R' is BOC or CBZ.

26. A compound of formula VI, or a pharmaceutically acceptable salt thereof,

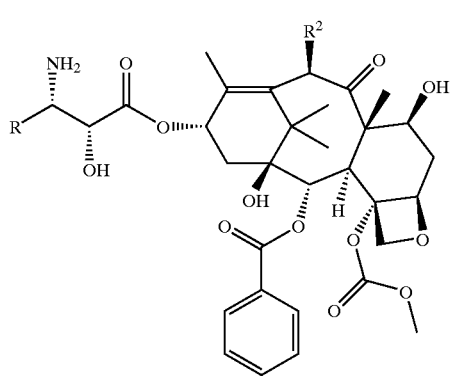

VI wherein:

R is phenyl, isopropyl, or tert butyl; and $R^2$ is $CH_3C(O)O$—.

27. The compound of claim 26, wherein R is tert butyl.

28. A process for the preparation of a metal alkoxide of formula IIm,

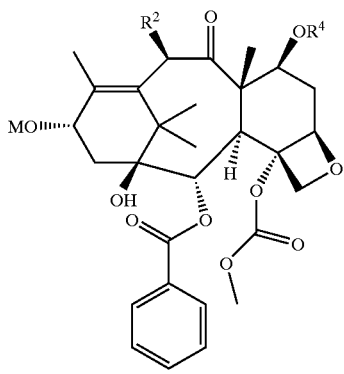

wherein $R^2$ is $CH_3C(O)O-$, $R^4$ is a hydroxy protecting group, and M is a metal atom (ion),
comprising reacting a compound of formula II,

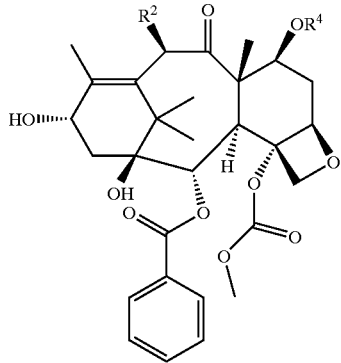

wherein $R^2$ and $R^4$ are as defined hereinabove,
with a metal base.

29. The process of claim 28, wherein said metal base is selected from the group consisting of lithium diisopropylamide, $C_{1-6}$ alkyllithium, lithium bis(trimethylsilyl)amide, sodium bis(trimethylsilyl)amide, potassium bis(trimethylsilyl)amide, phenyllithium, sodium hydride, potassium hydride and lithium hydride.

30. The process of claim 28, further comprising reacting said metal alkoxide of formula IIm with a beta-lactam of formula IV,

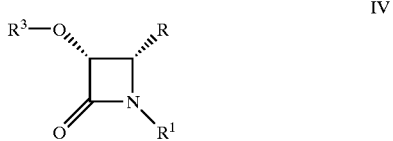

wherein:
R is phenyl, isopropyl, or tert butyl;
$R^1$ is $-C(O)R^Z$ in which $R^Z$ is $(CH_3)_3CO-$, $(CH_3)_3CCH_2-$, $CH_3(CH_2)_3O-$, cyclobutyl-, cyclohexyloxy, or (2-furyl); and
$R^3$ is a hydroxyl protecting group,
to produce a compound of formula III,

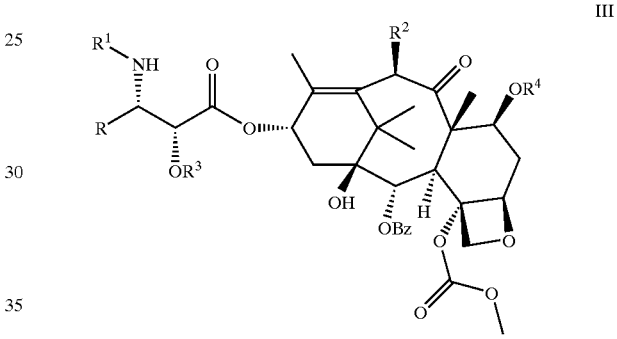

wherein R, $R^1$ and $R^3$ are as defined hereinabove; $R^2$ and $R^4$ are as defined in claim 28.

* * * * *

UNITED STATES PATENT AND TRADEMARK OFFICE
CERTIFICATE OF CORRECTION

PATENT NO. : 6,916,942 B2  Page 1 of 2
DATED : July 12, 2005
INVENTOR(S) : Kadow et al.

It is certified that error appears in the above-identified patent and that said Letters Patent is hereby corrected as shown below:

Column 11,
Lines 55-56, the structure shown should be:

-- 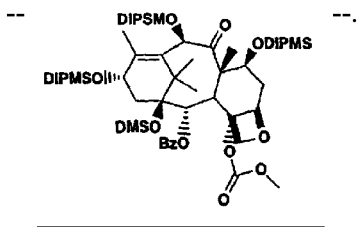 --.

Column 12,
Lines 1-15, the structure shown should be:

-- 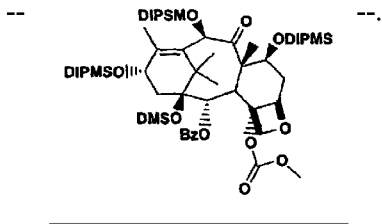 --.

Column 30,
Line 9, should read -- said carbonate hydroxy protecting group is methyl, ethyl, --.

UNITED STATES PATENT AND TRADEMARK OFFICE
CERTIFICATE OF CORRECTION

PATENT NO. : 6,916,942 B2
DATED : July 12, 2005
INVENTOR(S) : Kadow et al.

It is certified that error appears in the above-identified patent and that said Letters Patent is hereby corrected as shown below:

<u>Column 31,</u>
Line 38, should read -- 8. The process of claim 7, wherein said hydroxy protect- --.
Line 43, should read -- said ether hydroxy protecting group is methyl, t-butyl, --.
Line 48, should read -- said dialkysilylether hydroxy protecting group is dim- --.
Line 50, should read -- said trialkylsilylether hydroxy protecting group is --.
Line 52, should read -- said dialkylalkoxysilylether hydroxy protecting group is --.
Line 54, should read -- said ester hydroxy protecting group is benzoyl, acetyl, --.
Line 56, should read -- said carbonate hydroxy protecting group is methyl, ethyl, --.

Signed and Sealed this

Sixth Day of June, 2006

JON W. DUDAS
*Director of the United States Patent and Trademark Office*